United States Patent
Hong et al.

(10) Patent No.: US 11,359,219 B2
(45) Date of Patent: Jun. 14, 2022

(54) TRANSAMINASE MUTANT AND APPLICATION THEREOF

(71) Applicant: ASYMCHEM LIFE SCIENCE (TIANJIN) CO., LTD, Tianjin (CN)

(72) Inventors: Hao Hong, Morrisville, NC (US); Gage James, Morrisville, NC (US); Jiangping Lu, Tianjin (CN); Xingfu Xu, Tianjin (CN); Yuxia Cui, Tianjin (CN); Na Zhang, Tianjin (CN); Xuewu Dong, Tianjin (CN); Wenyan Yu, Tianjin (CN); Xin Huang, Tianjin (CN); Mingmin Hao, Tianjin (CN); Yulei Ma, Tianjin (CN); Yibing Cheng, Tianjin (CN); Jiadong Zhao, Tianjin (CN)

(73) Assignee: ASYMCHEM LIFE SCIENCE (TIANJIN) CO., LTD, Tianjin (CN)

( * ) Notice: Subject to any disclaimer, the term of this patent is extended or adjusted under 35 U.S.C. 154(b) by 0 days.

(21) Appl. No.: 16/966,528

(22) PCT Filed: Feb. 5, 2018

(86) PCT No.: PCT/CN2018/075272
§ 371 (c)(1),
(2) Date: Jul. 31, 2020

(87) PCT Pub. No.: WO2019/148494
PCT Pub. Date: Aug. 8, 2019

(65) Prior Publication Data
US 2021/0054428 A1    Feb. 25, 2021

(51) Int. Cl.
| C12P 17/12 | (2006.01) |
| C12P 17/10 | (2006.01) |
| C12N 9/10  | (2006.01) |
| C12N 11/082 | (2020.01) |
| C12N 11/00 | (2006.01) |
| C12N 11/10 | (2006.01) |

(52) U.S. Cl.
CPC .......... *C12P 17/12* (2013.01); *C12N 9/1096* (2013.01); *C12N 11/00* (2013.01); *C12N 11/082* (2020.01); *C12N 11/10* (2013.01); *C12P 17/10* (2013.01)

(58) Field of Classification Search
CPC ......... C12P 13/00; C12P 19/26; C12P 13/001; C12N 15/67; C12N 9/1096; C12Y 206/01
USPC .... 435/193, 189, 252.3, 320.1, 15, 108, 109
See application file for complete search history.

(56) References Cited

U.S. PATENT DOCUMENTS

2013/0305398 A1   11/2013  Coffin
2016/0298092 A1   10/2016  Shin

FOREIGN PATENT DOCUMENTS

| CN | 102341494 A | 2/2012 |
| CN | 104894148 A | 9/2015 |
| CN | 106676142 A | 5/2017 |
| JP | 2014524245 A | 9/2014 |
| WO | 2009134339 A8 | 4/2009 |
| WO | 2009134334 A2 | 11/2009 |
| WO | 2016106247 A1 | 6/2016 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
International Search Report for corresponding application PCT/CN2018/075272 filed Feb. 5, 2018; dated Nov. 7, 2018.
European Search Report for corresponding application EP 18 90 3278; Report dated Nov. 12, 2021.
Maria S. Humble, "Crystal Structures of the Chromobacterium violaceum transaminase reveal major structure rearrangements upon binding of coenzyme PLP" FEBS Journal 279 (2012).
Sarah Almahboub, "Single Point Mutations reveal amino Acid residues important for Chromobacterium violaceum transaminase activity in the production of unnatural amino acids", Scientific Reports, (2018).

* cited by examiner

*Primary Examiner* — Robert B Mondesi
*Assistant Examiner* — Mohammad Y Meah
(74) *Attorney, Agent, or Firm* — Cantor Colburn LLP

(57) ABSTRACT

The invention provides a transaminase mutant and application thereof, wherein the amino acid sequence of the transaminase mutant is formed after mutation of the amino acid sequence as shown in SEQ ID NO: 1, and mutated amino acid sites comprise T7C+S47C sites. The transaminase mutant having the mutation sites can be further prepared into an immobilized enzyme through an immobilization technology, the immobilized enzyme has relatively high activity and high stability, can be recycled for multiple times, and is applicable to continuous flow reaction in a packed bed.

18 Claims, No Drawings
Specification includes a Sequence Listing.

SEQUENCE LISTING

```
<160> NUMBER OF SEQ ID NOS: 56

<210> SEQ ID NO 1
<211> LENGTH: 459
<212> TYPE: PRT
<213> ORGANISM: Chromobacterium violaceum

<400> SEQUENCE: 1

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
```

```
                100             105             110
Arg Val Phe Tyr Thr Asn Ser Gly Ser Glu Ser Val Asp Thr Met Ile
            115             120             125

Arg Met Val Arg Arg Tyr Trp Asp Val Gln Gly Lys Pro Glu Lys Lys
            130             135             140

Thr Leu Ile Gly Arg Trp Asn Gly Tyr His Gly Ser Thr Ile Gly Gly
145             150             155             160

Ala Ser Leu Gly Gly Met Lys Tyr Met His Glu Gln Gly Asp Leu Pro
            165             170             175

Ile Pro Gly Met Ala His Ile Glu Gln Pro Trp Trp Tyr Lys His Gly
            180             185             190

Lys Asp Met Thr Pro Asp Glu Phe Gly Val Val Ala Ala Arg Trp Leu
            195             200             205

Glu Glu Lys Ile Leu Glu Ile Gly Ala Asp Lys Val Ala Ala Phe Val
            210             215             220

Gly Glu Pro Ile Gln Gly Ala Gly Gly Val Ile Val Pro Pro Ala Thr
225             230             235             240

Tyr Trp Pro Glu Ile Glu Arg Ile Cys Arg Lys Tyr Asp Val Leu Leu
            245             250             255

Val Ala Asp Glu Val Ile Cys Gly Phe Gly Arg Thr Gly Glu Trp Phe
            260             265             270

Gly His Gln His Phe Gly Phe Gln Pro Asp Leu Phe Thr Ala Ala Lys
            275             280             285

Gly Leu Ser Ser Gly Tyr Leu Pro Ile Gly Ala Val Phe Val Gly Lys
            290             295             300

Arg Val Ala Glu Gly Leu Ile Ala Gly Gly Asp Phe Asn His Gly Phe
305             310             315             320

Thr Tyr Ser Gly His Pro Val Cys Ala Ala Val Ala His Ala Asn Val
            325             330             335

Ala Ala Leu Arg Asp Glu Gly Ile Val Gln Arg Val Lys Asp Asp Ile
            340             345             350

Gly Pro Tyr Met Gln Lys Arg Trp Arg Glu Thr Phe Ser Arg Phe Glu
            355             360             365

His Val Asp Asp Val Arg Gly Val Gly Met Val Gln Ala Phe Thr Leu
            370             375             380

Val Lys Asn Lys Ala Lys Arg Glu Leu Phe Pro Asp Phe Gly Glu Ile
385             390             395             400

Gly Thr Leu Cys Arg Asp Ile Phe Phe Arg Asn Asn Leu Ile Met Thr
            405             410             415

Ala Cys Gly Asp His Ile Val Ser Ala Pro Pro Leu Val Met Thr Arg
            420             425             430

Ala Glu Val Asp Glu Met Leu Ala Val Ala Glu Arg Cys Leu Glu Glu
            435             440             445

Phe Glu Gln Thr Leu Lys Ala Arg Gly Leu Ala
            450             455

<210> SEQ ID NO 2
<211> LENGTH: 459
<212> TYPE: PRT
<213> ORGANISM: Chromobacterium violaceum

<400> SEQUENCE: 2

Met Gln Lys Gln Arg Thr Cys Ser Gln Trp Arg Glu Leu Asp Ala Ala
1               5                   10                  15
```

-continued

```
His His Leu His Pro Phe Thr Asp Thr Ala Ser Leu Asn Gln Ala Gly
             20                  25                  30

Ala Arg Val Met Thr Arg Gly Glu Gly Val Tyr Leu Trp Asp Cys Glu
         35                  40                  45

Gly Asn Lys Ile Ile Asp Gly Met Ala Gly Leu Trp Cys Val Asn Val
 50                  55                  60

Gly Tyr Gly Arg Lys Asp Phe Ala Glu Ala Arg Arg Gln Met Glu
 65                  70                  75                  80

Glu Leu Pro Phe Tyr Asn Thr Phe Phe Lys Thr Thr His Pro Ala Val
                 85                  90                  95

Val Glu Leu Ser Ser Leu Leu Ala Glu Val Thr Pro Ala Gly Phe Asp
             100                 105                 110

Arg Val Phe Tyr Thr Asn Ser Gly Ser Glu Ser Val Asp Thr Met Ile
         115                 120                 125

Arg Met Val Arg Arg Tyr Trp Asp Val Gln Gly Lys Pro Glu Lys Lys
     130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                 165                 170                 175

Ile Pro Gly Met Ala His Ile Glu Gln Pro Trp Trp Tyr Lys His Gly
             180                 185                 190

Lys Asp Met Thr Pro Asp Glu Phe Gly Val Val Ala Ala Arg Trp Leu
         195                 200                 205

Glu Glu Lys Ile Leu Glu Ile Gly Ala Asp Lys Val Ala Ala Phe Val
     210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                 245                 250                 255

Val Ala Asp Glu Val Ile Cys Gly Phe Gly Arg Thr Gly Glu Trp Phe
         260                 265                 270

Gly His Gln His Phe Gly Phe Gln Pro Asp Leu Phe Thr Ala Ala Lys
     275                 280                 285

Gly Leu Ser Ser Gly Tyr Leu Pro Ile Gly Ala Val Phe Val Gly Lys
 290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                 325                 330                 335

Ala Ala Leu Arg Asp Glu Gly Ile Val Gln Arg Val Lys Asp Ile
         340                 345                 350

Gly Pro Tyr Met Gln Lys Arg Trp Arg Glu Thr Phe Ser Arg Phe Glu
     355                 360                 365

His Val Asp Asp Val Arg Gly Val Gly Met Val Gln Ala Phe Thr Leu
 370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                 405                 410                 415

Ala Cys Gly Asp His Ile Val Ser Ala Pro Pro Leu Val Met Thr Arg
         420                 425                 430

Ala Glu Val Asp Glu Met Leu Ala Val Ala Glu Arg Cys Leu Glu Glu
```

```
              435                 440                 445
    Phe Glu Gln Thr Leu Lys Ala Arg Gly Leu Ala
        450                 455

<210> SEQ ID NO 3
<211> LENGTH: 459
<212> TYPE: PRT
<213> ORGANISM: Chromobacterium violaceum

<400> SEQUENCE: 3

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350
```

```
Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 4
<211> LENGTH: 459
<212> TYPE: PRT
<213> ORGANISM: Chromobacterium violaceum

<400> SEQUENCE: 4

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Thr Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270
```

```
Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
450                 455

<210> SEQ ID NO 5
<211> LENGTH: 459
<212> TYPE: PRT
<213> ORGANISM: Chromobacterium violaceum

<400> SEQUENCE: 5

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65              70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
```

```
            180                 185                 190
Lys Asp Met Thr Pro Asp Glu Phe Gly Val Ala Ala Arg Trp Leu
            195                 200                 205
Glu Glu Lys Ile Leu Glu Ile Gly Ala Asp Lys Val Ala Phe Val
            210                 215                 220
Gly Glu Pro Ile Gln Gly Ala Gly Val Ile Val Pro Pro Ala Thr
225                 230                 235                 240
Tyr Trp Pro Glu Ile Glu Arg Ile Cys Arg Lys Tyr Asp Val Leu Leu
                    245                 250                 255
Val Ala Asp Glu Val Ile Cys Gly Phe Gly Arg Thr Gly Glu Trp Phe
                    260                 265                 270
Gly His Gln His Phe Gly Phe Gln Pro Asp Leu Phe Thr Ala Ala Lys
            275                 280                 285
Gly Leu Ser Ser Gly Tyr Leu Pro Ile Gly Ala Val Phe Val Gly Lys
            290                 295                 300
Arg Val Ala Glu Gly Leu Ile Ala Gly Gly Asp Phe Asn His Gly Phe
305                 310                 315                 320
Thr Tyr Ser Gly His Pro Val Cys Ala Ala Val Ala His Ala Asn Val
                    325                 330                 335
Ala Ala Leu Arg Asp Glu Gly Ile Val Gln Arg Val Lys Asp Asp Ile
                    340                 345                 350
Gly Pro Tyr Met Gln Lys Arg Trp Arg Glu Thr Phe Ser Arg Phe Glu
            355                 360                 365
His Val Asp Asp Val Arg Gly Val Gly Met Val Gln Ala Phe Thr Leu
            370                 375                 380
Val Lys Asn Lys Ala Lys Arg Glu Leu Phe Pro Asp Phe Gly Glu Ile
385                 390                 395                 400
Gly Thr Leu Cys Arg Asp Ile Phe Phe Arg Asn Asn Leu Ile Met Thr
                    405                 410                 415
Ala Cys Gly Asp His Ile Val Ser Ala Pro Pro Leu Val Leu Thr Arg
                    420                 425                 430
Ala Glu Val Asp Glu Met Leu Ala Val Ala Glu Arg Cys Leu Glu Glu
            435                 440                 445
Phe Glu Gln Thr Leu Lys Ala Arg Gly Leu Ala
            450                 455

<210> SEQ ID NO 6
<211> LENGTH: 459
<212> TYPE: PRT
<213> ORGANISM: Chromobacterium violaceum

<400> SEQUENCE: 6

Met Gln Lys Gln Arg Thr Cys Ser Gln Trp Arg Glu Leu Asp Ala Ala
1               5                   10                  15
His His Leu His Pro Phe Thr Asp Thr Ala Ser Leu Asn Gln Ala Gly
            20                  25                  30
Ala Arg Val Met Thr Arg Gly Glu Gly Val Tyr Leu Trp Asp Cys Glu
            35                  40                  45
Gly Asn Arg Ile Ile Asp Gly Met Ala Gly Leu Trp Cys Val Asn Val
            50                  55                  60
Gly Tyr Gly Arg Lys Asp Phe Ala Glu Ala Ala Arg Arg Gln Met Glu
65              70                  75                  80
Glu Leu Pro Phe Tyr Asn Thr Phe Phe Lys Thr Thr His Pro Ala Val
            85                  90                  95
```

```
Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 7
<211> LENGTH: 459
<212> TYPE: PRT
<213> ORGANISM: Chromobacterium violaceum

<400> SEQUENCE: 7

Met Gln Lys Gln Arg Thr Cys Ser Gln Trp Arg Glu Leu Asp Ala Ala
1               5                   10                  15
```

-continued

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
 50                  55                  60

Gly Tyr Gly Arg Lys Asp Phe Ala Glu Ala Ala Arg Arg Gln Met Glu
 65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Leu Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

```
Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 8
<211> LENGTH: 459
<212> TYPE: PRT
<213> ORGANISM: Chromobacterium violaceum

<400> SEQUENCE: 8

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350
```

-continued

Gly Pro Tyr Leu Gln Lys Arg Trp Arg Glu Thr Phe Ser Arg Phe Glu
          355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
                435                 440                 445

Phe Glu Gln Thr Leu Lys Ala Arg Gly Leu Ala
                450                 455

<210> SEQ ID NO 9
<211> LENGTH: 459
<212> TYPE: PRT
<213> ORGANISM: Chromobacterium violaceum

<400> SEQUENCE: 9

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe

```
                    260                 265                 270
Gly His Gln His Phe Gly Phe Gln Pro Asp Leu Phe Thr Ala Ala Lys
            275                 280                 285
Gly Leu Ser Ser Gly Tyr Leu Pro Ile Gly Ala Val Phe Val Gly Lys
            290                 295                 300
Arg Val Ala Glu Gly Leu Ile Ala Gly Gly Asp Phe Asn His Gly Phe
305                 310                 315                 320
Thr Tyr Ser Gly His Pro Val Cys Ala Ala Val Ala His Ala Asn Val
                325                 330                 335
Ala Ala Leu Arg Asp Glu Gly Ile Val Gln Arg Val Lys Asp Asp Ile
                340                 345                 350
Gly Pro Tyr Met Gln Lys Arg Trp Arg Glu Thr Leu Ser Arg Phe Glu
            355                 360                 365
His Val Asp Asp Val Arg Gly Val Gly Met Val Gln Ala Phe Thr Leu
            370                 375                 380
Val Lys Asn Lys Ala Lys Arg Glu Leu Phe Pro Asp Phe Gly Glu Ile
385                 390                 395                 400
Gly Thr Leu Cys Arg Asp Ile Phe Phe Arg Asn Asn Leu Ile Met Thr
                405                 410                 415
Ala Cys Gly Asp His Ile Val Ser Ala Pro Pro Leu Val Met Thr Arg
                420                 425                 430
Ala Glu Val Asp Glu Met Leu Ala Val Ala Glu Arg Cys Leu Glu Glu
            435                 440                 445
Phe Glu Gln Thr Leu Lys Ala Arg Gly Leu Ala
            450                 455

<210> SEQ ID NO 10
<211> LENGTH: 459
<212> TYPE: PRT
<213> ORGANISM: Chromobacterium violaceum

<400> SEQUENCE: 10

Met Gln Lys Gln Arg Thr Cys Ser Gln Trp Arg Glu Leu Asp Ala Ala
1               5                   10                  15
His His Leu His Pro Phe Thr Asp Thr Ala Ser Leu Asn Gln Ala Gly
                20                  25                  30
Ala Arg Val Met Thr Arg Gly Glu Gly Val Tyr Leu Trp Asp Cys Glu
            35                  40                  45
Gly Asn Lys Ile Ile Asp Gly Met Ala Gly Leu Trp Cys Val Asn Val
    50                  55                  60
Gly Tyr Gly Arg Lys Asp Phe Ala Glu Ala Ala Arg Arg Gln Met Glu
65                  70                  75                  80
Glu Leu Pro Phe Tyr Asn Thr Phe Phe Lys Thr Thr His Pro Ala Val
                85                  90                  95
Val Glu Leu Ser Ser Leu Leu Ala Glu Val Thr Pro Ala Gly Phe Asp
                100                 105                 110
Arg Val Phe Tyr Thr Asn Ser Gly Ser Glu Ser Val Asp Thr Met Ile
            115                 120                 125
Arg Met Val Arg Arg Tyr Trp Asp Val Gln Gly Lys Pro Glu Lys Lys
        130                 135                 140
Thr Leu Ile Gly Arg Trp Asn Gly Tyr His Gly Ser Thr Ile Gly Gly
145                 150                 155                 160
Ala Ser Leu Gly Gly Met Lys Tyr Met His Glu Gln Gly Asp Leu Pro
                165                 170                 175
```

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
        260                 265                 270

Gly His Gln His Phe Gly Phe Gln Pro Asp Leu Phe Thr Ala Ala Lys
    275                 280                 285

Gly Leu Ser Ser Gly Tyr Leu Pro Ile Gly Ala Val Phe Val Gly Lys
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
        340                 345                 350

Gly Pro Tyr Met Gln Lys Arg Trp Arg Glu Thr Phe Ser Arg Phe Glu
    355                 360                 365

His Val Gly Asp Val Arg Gly Val Gly Met Val Gln Ala Phe Thr Leu
370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
            405                 410                 415

Ala Cys Gly Asp His Ile Val Ser Ala Pro Pro Leu Val Met Thr Arg
        420                 425                 430

Ala Glu Val Asp Glu Met Leu Ala Val Ala Glu Arg Cys Leu Glu Glu
    435                 440                 445

Phe Glu Gln Thr Leu Lys Ala Arg Gly Leu Ala
450                 455

<210> SEQ ID NO 11
<211> LENGTH: 459
<212> TYPE: PRT
<213> ORGANISM: Chromobacterium violaceum

<400> SEQUENCE: 11

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Pro Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 12
<211> LENGTH: 459
<212> TYPE: PRT
<213> ORGANISM: Chromobacterium violaceum

<400> SEQUENCE: 12

Met Gln Lys Gln Arg Thr Cys Ser Gln Trp Arg Glu Leu Asp Ala Ala

-continued

```
1               5                   10                  15
His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
            50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Ala Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430
```

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 13
<211> LENGTH: 459
<212> TYPE: PRT
<213> ORGANISM: Chromobacterium violaceum

<400> SEQUENCE: 13

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Ala Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile

```
              340                 345                 350
Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
        370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
            450                 455

<210> SEQ ID NO 14
<211> LENGTH: 459
<212> TYPE: PRT
<213> ORGANISM: Chromobacterium violaceum

<400> SEQUENCE: 14

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255
```

-continued

```
Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala Lys Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 15
<211> LENGTH: 459
<212> TYPE: PRT
<213> ORGANISM: Chromobacterium violaceum

<400> SEQUENCE: 15

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
            50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Pro Val
            85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
            165                 170                 175
```

```
Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
450                 455

<210> SEQ ID NO 16
<211> LENGTH: 459
<212> TYPE: PRT
<213> ORGANISM: Chromobacterium violaceum

<400> SEQUENCE: 16

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
            50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
```

```
            85                  90                  95
Val Glu Leu Ser Ser Leu Leu Ala Glu Val Thr Pro Ala Pro Phe Asp
            100                 105                 110

Arg Val Phe Tyr Thr Asn Ser Gly Ser Glu Val Asp Thr Met Ile
        115                 120                 125

Arg Met Val Arg Arg Tyr Trp Asp Val Gln Gly Lys Pro Glu Lys Lys
        130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
        210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
        290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
        370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
450                 455

<210> SEQ ID NO 17
<211> LENGTH: 459
<212> TYPE: PRT
<213> ORGANISM: Chromobacterium violaceum

<400> SEQUENCE: 17
```

-continued

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65              70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Asp
        290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
        370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
```

```
                    420             425             430
Ala Glu Val Asp Glu Met Leu Ala Val Ala Glu Arg Cys Leu Glu Glu
                435             440             445

Phe Glu Gln Thr Leu Lys Ala Arg Gly Leu Ala
    450             455

<210> SEQ ID NO 18
<211> LENGTH: 459
<212> TYPE: PRT
<213> ORGANISM: Chromobacterium violaceum

<400> SEQUENCE: 18

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Cys Glu
                35                  40                  45

Gly Asn Lys Ile Ile Asp Gly Met Ala Gly Leu Trp Cys Val Asn Val
            50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Phe Pro Ala Gly Phe Asp
                100                 105                 110

Arg Val Phe Tyr Thr Asn Ser Gly Ser Glu Ser Val Asp Thr Met Ile
                115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
                180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
                210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
                260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
                290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335
```

```
Ala Ala Leu Arg Asp Glu Gly Ile Val Gln Arg Val Lys Asp Ile
            340                 345                 350

Gly Pro Tyr Met Gln Lys Arg Trp Arg Glu Thr Phe Ser Arg Phe Glu
355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 19
<211> LENGTH: 459
<212> TYPE: PRT
<213> ORGANISM: Chromobacterium violaceum

<400> SEQUENCE: 19

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255
```

-continued

```
Val Ala Asp Glu Val Ile Cys Gly Phe Gly Arg Thr Gly Glu Trp Phe
        260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
        290                 295                 300

Arg Val Ala Glu Gly Leu Ile Ala Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Pro
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
        450                 455

<210> SEQ ID NO 20
<211> LENGTH: 459
<212> TYPE: PRT
<213> ORGANISM: Chromobacterium violaceum

<400> SEQUENCE: 20

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
```

165                 170                 175
Ile Pro Gly Met Ala His Ile Glu Gln Pro Trp Trp Tyr Lys His Gly
            180                 185                 190

Lys Asp Met Thr Pro Asp Glu Phe Gly Val Val Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
        290                 295                 300

Arg Val Ala Glu Gly Leu Ile Ala Gly Gly Asp Phe Asn His Gly Phe
305                 310                 315                 320

Thr Tyr Ser Gly His Pro Val Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
        450                 455

<210> SEQ ID NO 21
<211> LENGTH: 459
<212> TYPE: PRT
<213> ORGANISM: Chromobacterium violaceum

<400> SEQUENCE: 21

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                 85                  90                  95

Val Glu Leu Ser Ser Leu Leu Ala Glu Val Ala Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
                180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 22
<211> LENGTH: 459
<212> TYPE: PRT
<213> ORGANISM: Chromobacterium violaceum

<400> SEQUENCE: 22

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
50                      55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415
```

```
Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 23
<211> LENGTH: 459
<212> TYPE: PRT
<213> ORGANISM: Chromobacterium violaceum

<400> SEQUENCE: 23

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
        130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335
```

```
Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Gly Leu Ile Met Thr
                405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455
```

<210> SEQ ID NO 24
<211> LENGTH: 459
<212> TYPE: PRT
<213> ORGANISM: Chromobacterium violaceum

<400> SEQUENCE: 24

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
            50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
            85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
```

```
            245                 250                 255
Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Glu Arg Val Lys Asp Asp Ile
                340                 345                 350

Gly Pro Tyr Met Gln Lys Arg Trp Arg Glu Thr Phe Ser Arg Phe Glu
                355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
                435                 440                 445

Phe Glu Gln Thr Leu Lys Ala Arg Gly Leu Ala
            450                 455

<210> SEQ ID NO 25
<211> LENGTH: 459
<212> TYPE: PRT
<213> ORGANISM: Chromobacterium violaceum

<400> SEQUENCE: 25

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160
```

```
Ala Ser Leu Gly Gly Met Lys Tyr Met His Glu Gln Gly Asp Leu Pro
            165                 170                 175

Ile Pro Gly Met Ala His Ile Glu Gln Pro Trp Trp Tyr Lys His Gly
        180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
        210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
        260                 265                 270

Gly His Gln His Phe Gly Phe Gln Pro Asp Leu Phe Thr Thr Ala Lys
            275                 280                 285

Gly Leu Ser Ser Gly Tyr Leu Pro Leu Gly Ala Val Phe Val Gly Asp
        290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
        340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Leu Ala Phe Thr Leu
        370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
            405                 410                 415

Ala Cys Gly Asp His Ile Val Ser Ala Pro Pro Leu Val Met Thr Arg
        420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
        450                 455

<210> SEQ ID NO 26
<211> LENGTH: 459
<212> TYPE: PRT
<213> ORGANISM: Chromobacterium violaceum

<400> SEQUENCE: 26

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80
```

Glu Leu Pro Phe Tyr Asn Thr Phe Phe Gly Thr Thr His Pro Pro Val
                    85                  90                  95

Val Glu Leu Ser Ser Leu Leu Ala Glu Val Thr Pro Ala Gly Phe Asp
                100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
        130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
                180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
        210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Leu Gly Ala Val Phe Val Gly Asp
        290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Pro
        355                 360                 365

His Val Asp Asp Val Arg Gly Val Gly Met Val Leu Ala Phe Thr Leu
        370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 27
<211> LENGTH: 459
<212> TYPE: PRT
<213> ORGANISM: Chromobacterium violaceum

```
<400> SEQUENCE: 27

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Tyr Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415
```

```
Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455
```

<210> SEQ ID NO 28
<211> LENGTH: 459
<212> TYPE: PRT
<213> ORGANISM: Chromobacterium violaceum

<400> SEQUENCE: 28

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
 50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
            85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
            165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
```

```
            325                 330                 335
Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Leu Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 29
<211> LENGTH: 459
<212> TYPE: PRT
<213> ORGANISM: Chromobacterium violaceum

<400> SEQUENCE: 29

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
            85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
            165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240
```

```
Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Leu Gly Ala Val Phe Val Gly Lys
    290                 295                 300

Arg Val Ala Glu Gly Leu Ile Ala Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 30
<211> LENGTH: 459
<212> TYPE: PRT
<213> ORGANISM: Chromobacterium violaceum

<400> SEQUENCE: 30

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
    50                  55                  60

Gly Tyr Gly Arg Asn Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
    115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160
```

```
Ala Ser Leu Gly Gly Met Lys Tyr Met His Glu Gln Gly Asp Leu Pro
            165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 31
<211> LENGTH: 459
<212> TYPE: PRT
<213> ORGANISM: Chromobacterium violaceum

<400> SEQUENCE: 31

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
            50                  55                  60

Gly Tyr Gly Arg Lys Asp Phe Ala Glu Ala Ala Arg Arg Gln Met Glu
```

```
              65                  70                  75                  80
Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Ile Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 32
<211> LENGTH: 459
<212> TYPE: PRT
<213> ORGANISM: Chromobacterium violaceum
```

<400> SEQUENCE: 32

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Glu His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
```

```
                    405                 410                 415
Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
        450                 455

<210> SEQ ID NO 33
<211> LENGTH: 459
<212> TYPE: PRT
<213> ORGANISM: Chromobacterium violaceum

<400> SEQUENCE: 33

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

His Val Ala Glu Gly Leu Ile Ala Gly Gly Asp Phe Asn His Gly Phe
305                 310                 315                 320
```

```
Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
            405                 410                 415

Ala Cys Gly Asp His Ile Val Ser Ala Pro Pro Leu Val Met Thr Arg
        420                 425                 430

Ala Glu Val Asp Glu Met Leu Ala Val Ala Glu Arg Cys Leu Glu Glu
    435                 440                 445

Phe Glu Gln Thr Leu Lys Ala Arg Gly Leu Ala
    450                 455

<210> SEQ ID NO 34
<211> LENGTH: 459
<212> TYPE: PRT
<213> ORGANISM: Chromobacterium violaceum

<400> SEQUENCE: 34

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240
```

```
Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Thr Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 35
<211> LENGTH: 459
<212> TYPE: PRT
<213> ORGANISM: Chromobacterium violaceum

<400> SEQUENCE: 35

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
```

Ala Ser Leu Gly Gly Met Lys Tyr Met His Glu Gln Gly Asp Leu Pro
145                 150                 155                 160

Ile Pro Gly Met Ala His Ile Glu Gln Pro Trp Trp Tyr Lys His Gly
            165                 170                 175

Lys Asp Met Thr Pro Asp Glu Phe Cys Val Val Ala Ala Arg Trp Leu
        180                 185                 190

Glu Glu Lys Ile Leu Glu Ile Gly Ala Asp Lys Val Ala Ala Phe Val
    195                 200                 205

Gly Glu Pro Ile Gln Gly Ala Gly Val Ile Val Pro Pro Ala Thr
210                 215                 220

Tyr Trp Pro Glu Ile Glu Arg Ile Cys Arg Lys Tyr Asp Val Leu Leu
225                 230                 235                 240

Val Ala Asp Glu Val Ile Cys Gly Phe Gly Arg Thr Gly Glu Trp Phe
            245                 250                 255

Gly His Gln His Phe Gly Phe Gln Pro Asp Leu Phe Thr Ala Ala Lys
        260                 265                 270

Gly Leu Ser Ser Gly Tyr Leu Pro Ile Gly Ala Val Phe Val Gly Lys
    275                 280                 285

Arg Val Ala Glu Gly Leu Ile Ala Gly Gly Asp Phe Asn His Gly Phe
290                 295                 300

Thr Tyr Ser Gly His Pro Val Cys Ala Ala Val Ala His Ala Asn Val
305                 310                 315                 320

Ala Ala Leu Arg Asp Glu Gly Ile Val Gln Arg Val Lys Asp Asp Ile
            325                 330                 335

Gly Pro Tyr Met Gln Lys Arg Trp Arg Glu Thr Phe Ser Arg Phe Glu
        340                 345                 350

His Val Asp Asp Val Arg Gly Val Gly Met Val Gln Ala Phe Thr Leu
    355                 360                 365

Val Lys Asn Lys Ala Lys Arg Glu Leu Phe Pro Asp Phe Gly Glu Ile
370                 375                 380

Gly Thr Leu Cys Arg Asp Ile Phe Phe Arg Asn Asn Leu Ile Met Thr
385                 390                 395                 400

Ala Cys Gly Asp His Ile Val Ser Ala Pro Pro Leu Val Met Thr Arg
            405                 410                 415

Ala Glu Val Asp Glu Met Leu Ala Val Ala Glu Arg Cys Leu Glu Glu
        420                 425                 430

Phe Glu Gln Thr Leu Lys Ala Arg Gly Leu Ala
    435                 440                 445

<210> SEQ ID NO 36
<211> LENGTH: 459
<212> TYPE: PRT
<213> ORGANISM: Chromobacterium violaceum

<400> SEQUENCE: 36

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Arg Ile Ile Asp Gly Met Ala Gly Leu Trp Cys Val Asn Val
    50                  55                  60

Gly Tyr Gly Arg Lys Asp Phe Ala Glu Ala Arg Arg Gln Met Glu
 65                  70                  75                  80

Glu Leu Pro Phe Tyr Asn Thr Phe Phe Lys Thr Thr His Pro Ala Val
                 85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Tyr Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
450                 455

<210> SEQ ID NO 37
<211> LENGTH: 459
<212> TYPE: PRT

<213> ORGANISM: Chromobacterium violaceum

<400> SEQUENCE: 37

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Pro Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Asp
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
370                 375                 380

Val Lys Asn Lys Ala Lys Arg Glu Leu Phe Pro Asp Phe Gly Glu Ile
385                 390                 395                 400
```

```
Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
450                 455

<210> SEQ ID NO 38
<211> LENGTH: 459
<212> TYPE: PRT
<213> ORGANISM: Chromobacterium violaceum

<400> SEQUENCE: 38

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Pro Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
        130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Asp
    290                 295                 300

Arg Val Ala Glu Gly Leu Ile Ala Gly Gly Asp Phe Asn His Gly Phe
305                 310                 315                 320
```

```
Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Leu Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 39
<211> LENGTH: 459
<212> TYPE: PRT
<213> ORGANISM: Chromobacterium violaceum

<400> SEQUENCE: 39

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
            50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
            85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
            165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
```

```
                225                 230                 235                 240
Tyr Trp Pro Glu Ile Glu Arg Ile Cys Arg Lys Tyr Asp Val Leu Leu
                    245                 250                 255

Val Ala Asp Glu Val Ile Cys Gly Phe Gly Arg Thr Gly Glu Trp Phe
                260                 265                 270

Gly His Gln His Phe Gly Phe Gln Pro Asp Leu Phe Thr Ala Ala Lys
                275                 280                 285

Gly Leu Ser Ser Gly Tyr Leu Pro Ile Gly Ala Val Phe Val Gly Asp
                290                 295                 300

Arg Val Ala Glu Gly Leu Ile Ala Gly Asp Phe Asn His Gly Phe
305                 310                 315                 320

Thr Tyr Ser Gly His Pro Val Cys Ala Ala Val Ala His Ala Asn Val
                    325                 330                 335

Ala Ala Leu Arg Asp Glu Gly Ile Val Gln Arg Val Lys Asp Asp Ile
                340                 345                 350

Gly Pro Tyr Met Gln Lys Arg Trp Arg Glu Thr Phe Ser Arg Phe Glu
                355                 360                 365

His Val Asp Asp Val Arg Gly Val Gly Met Val Leu Ala Phe Thr Leu
                370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                    405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
                435                 440                 445

Phe Glu Gln Thr Leu Lys Ala Arg Gly Leu Ala
                450                 455

<210> SEQ ID NO 40
<211> LENGTH: 459
<212> TYPE: PRT
<213> ORGANISM: Chromobacterium violaceum

<400> SEQUENCE: 40

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Cys Glu
                35                  40                  45

Gly Asn Lys Ile Ile Asp Gly Met Ala Gly Leu Trp Cys Val Asn Val
                50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Thr Pro Ala Gly Phe Asp
                100                 105                 110

Arg Val Phe Tyr Thr Asn Ser Gly Ser Glu Ser Val Asp Thr Met Ile
                115                 120                 125

Arg Met Val Arg Arg Tyr Trp Asp Val Gln Gly Lys Pro Glu Lys Lys
                130                 135                 140
```

```
Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
            165                 170                 175

Ile Pro Gly Met Ala His Ile Glu Gln Pro Trp Trp Tyr Lys His Gly
                180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
            210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
                260                 265                 270

Gly His Gln His Phe Gly Phe Gln Pro Asp Leu Phe Thr Ala Ala Lys
                275                 280                 285

Gly Leu Ser Ser Gly Tyr Leu Pro Ile Gly Ala Val Phe Val Gly Asp
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Pro
            355                 360                 365

His Val Asp Asp Val Arg Gly Val Gly Met Val Leu Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 41
<211> LENGTH: 459
<212> TYPE: PRT
<213> ORGANISM: Chromobacterium violaceum

<400> SEQUENCE: 41

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
        50                  55                  60
```

Gly Tyr Gly Arg Lys Asp Phe Ala Glu Ala Arg Arg Gln Met Glu
65                  70                  75                  80

Glu Leu Pro Phe Tyr Asn Thr Phe Phe Gly Thr Thr His Pro Pro Val
            85                  90                  95

Val Glu Leu Ser Ser Leu Leu Ala Glu Val Thr Pro Ala Gly Phe Asp
                100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Asp
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Phe Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Leu Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
450                 455

<210> SEQ ID NO 42
<211> LENGTH: 459

<212> TYPE: PRT
<213> ORGANISM: Chromobacterium violaceum

<400> SEQUENCE: 42

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Asp
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala Lys Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Leu Ala Phe Thr Leu
    370                 375                 380

Val Lys Asn Lys Ala Lys Arg Glu Leu Phe Pro Asp Phe Gly Glu Ile
385                 390                 395                 400
```

```
Gly Thr Leu Cys Glu Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 43
<211> LENGTH: 459
<212> TYPE: PRT
<213> ORGANISM: Chromobacterium violaceum

<400> SEQUENCE: 43

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
            130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Asp
    290                 295                 300

Arg Val Ala Glu Gly Leu Ile Ala Gly Gly Asp Phe Asn His Gly Phe
```

```
                305                 310                 315                 320
Thr Tyr Ser Gly His Pro Val Cys Ala Ala Val Ala His Ala Asn Val
                        325                 330                 335

Ala Ala Leu Arg Asp Glu Gly Ile Val Gln Arg Val Lys Asp Asp Ile
                340                 345                 350

Gly Pro Tyr Met Gln Lys Arg Trp Arg Glu Thr Phe Ser Arg Phe Glu
                355                 360                 365

His Val Gly Asp Val Arg Gly Val Gly Met Val Leu Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                    405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 44
<211> LENGTH: 459
<212> TYPE: PRT
<213> ORGANISM: Chromobacterium violaceum

<400> SEQUENCE: 44

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Pro Val
                85                  90                  95

Val Glu Leu Ser Ser Leu Leu Ala Glu Val Thr Pro Ala Gly Phe Asp
                100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
        130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220
```

Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 45
<211> LENGTH: 459
<212> TYPE: PRT
<213> ORGANISM: Chromobacterium violaceum

<400> SEQUENCE: 45

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
            85                  90                  95

Val Glu Leu Ser Ser Leu Leu Ala Glu Val Thr Pro Ala Gly Phe Asp
        100                 105                 110

Arg Val Phe Tyr Thr Asn Ser Gly Ser Glu Ser Val Asp Thr Met Ile
    115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Ala Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Asp
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Leu Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 46
<211> LENGTH: 459
<212> TYPE: PRT
<213> ORGANISM: Chromobacterium violaceum

<400> SEQUENCE: 46

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val

```
            50                  55                  60
Gly Tyr Gly Arg Lys Asp Phe Ala Glu Ala Ala Arg Arg Gln Met Glu
 65                  70                  75                  80

Glu Leu Pro Phe Tyr Asn Thr Phe Gly Thr Thr His Pro Pro Val
                 85                  90                  95

Val Glu Leu Ser Ser Leu Leu Ala Glu Val Thr Pro Ala Gly Phe Asp
                100                 105                 110

Arg Val Phe Tyr Thr Asn Ser Gly Ser Glu Ser Val Asp Thr Met Ile
                115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
                180                 185                 190

Lys Asp Met Thr Pro Asp Glu Phe Gly Val Val Ala Ala Arg Trp Leu
                195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
                260                 265                 270

Gly His Gln His Phe Gly Phe Gln Pro Asp Leu Phe Thr Ala Ala Lys
                275                 280                 285

Gly Leu Ser Ser Gly Tyr Leu Pro Ile Gly Ala Val Phe Val Gly Asp
                290                 295                 300

Arg Val Ala Glu Gly Leu Ile Ala Gly Gly Asp Phe Asn His Gly Phe
305                 310                 315                 320

Thr Tyr Ser Gly His Pro Val Ala Ala Val Ala His Ala Asn Val
                325                 330                 335

Ala Ala Leu Arg Asp Glu Gly Ile Val Gln Arg Val Lys Asp Asp Ile
                340                 345                 350

Gly Pro Tyr Met Gln Lys Arg Trp Arg Glu Thr Phe Ser Arg Phe Glu
                355                 360                 365

His Val Asp Asp Val Arg Gly Val Gly Met Val Leu Ala Phe Thr Leu
                370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
                435                 440                 445

Phe Glu Gln Thr Leu Lys Ala Arg Gly Leu Ala
                450                 455

<210> SEQ ID NO 47
```

-continued

```
<211> LENGTH: 459
<212> TYPE: PRT
<213> ORGANISM: Chromobacterium violaceum

<400> SEQUENCE: 47
```

| Met | Gln | Lys | Gln | Arg | Thr | Cys | Ser | Gln | Trp | Arg | Glu | Leu | Asp | Ala | Ala |
|---|---|---|---|---|---|---|---|---|---|---|---|---|---|---|---|
| 1 | | | | 5 | | | | | 10 | | | | | 15 | |

| His | His | Leu | His | Pro | Phe | Thr | Asp | Thr | Ala | Ser | Leu | Asn | Gln | Ala | Gly |
|---|---|---|---|---|---|---|---|---|---|---|---|---|---|---|---|
| | | | 20 | | | | 25 | | | | 30 | | | | |

| Ala | Arg | Val | Met | Thr | Arg | Gly | Glu | Gly | Val | Tyr | Leu | Trp | Asp | Cys | Glu |
|---|---|---|---|---|---|---|---|---|---|---|---|---|---|---|---|
| | | | 35 | | | | | 40 | | | | | 45 | | |

| Gly | Asn | Lys | Ile | Ile | Asp | Gly | Met | Ala | Gly | Leu | Trp | Cys | Val | Asn | Val |
|---|---|---|---|---|---|---|---|---|---|---|---|---|---|---|---|
| | 50 | | | | | 55 | | | | | 60 | | | | |

| Gly | Tyr | Gly | Arg | Lys | Asp | Phe | Ala | Glu | Ala | Ala | Arg | Arg | Gln | Met | Glu |
|---|---|---|---|---|---|---|---|---|---|---|---|---|---|---|---|
| 65 | | | | | 70 | | | | | 75 | | | | | 80 |

| Glu | Leu | Pro | Phe | Tyr | Asn | Thr | Phe | Phe | Gly | Thr | Thr | His | Pro | Pro | Val |
|---|---|---|---|---|---|---|---|---|---|---|---|---|---|---|---|
| | | | | 85 | | | | | 90 | | | | | 95 | |

| Val | Glu | Leu | Ser | Ser | Leu | Leu | Ala | Glu | Val | Thr | Pro | Ala | Gly | Phe | Asp |
|---|---|---|---|---|---|---|---|---|---|---|---|---|---|---|---|
| | | | | 100 | | | | | 105 | | | | | 110 | |

| Arg | Val | Phe | Tyr | Thr | Asn | Ser | Gly | Ser | Glu | Ser | Val | Asp | Thr | Met | Ile |
|---|---|---|---|---|---|---|---|---|---|---|---|---|---|---|---|
| | | | 115 | | | | | 120 | | | | | 125 | | |

| Arg | Met | Val | Arg | Arg | Tyr | Trp | Asp | Val | Gln | Gly | Lys | Pro | Glu | Lys | Lys |
|---|---|---|---|---|---|---|---|---|---|---|---|---|---|---|---|
| 130 | | | | | 135 | | | | | 140 | | | | | |

| Thr | Leu | Ile | Gly | Arg | Trp | Asn | Gly | Tyr | His | Gly | Ser | Thr | Ile | Gly | Gly |
|---|---|---|---|---|---|---|---|---|---|---|---|---|---|---|---|
| 145 | | | | | 150 | | | | | 155 | | | | | 160 |

| Ala | Ser | Leu | Gly | Gly | Met | Lys | Tyr | Met | His | Glu | Gln | Gly | Asp | Leu | Pro |
|---|---|---|---|---|---|---|---|---|---|---|---|---|---|---|---|
| | | | | 165 | | | | | 170 | | | | | 175 | |

| Ile | Pro | Gly | Met | Ala | His | Ile | Glu | Gln | Pro | Trp | Trp | Tyr | Lys | His | Gly |
|---|---|---|---|---|---|---|---|---|---|---|---|---|---|---|---|
| | | | 180 | | | | | 185 | | | | | 190 | | |

| Lys | Asp | Met | Thr | Pro | Asp | Glu | Phe | Gly | Val | Val | Ala | Ala | Arg | Trp | Leu |
|---|---|---|---|---|---|---|---|---|---|---|---|---|---|---|---|
| | | | 195 | | | | | 200 | | | | | 205 | | |

| Glu | Glu | Lys | Ile | Leu | Glu | Ile | Gly | Ala | Asp | Lys | Val | Ala | Ala | Phe | Val |
|---|---|---|---|---|---|---|---|---|---|---|---|---|---|---|---|
| | 210 | | | | | 215 | | | | | 220 | | | | |

| Gly | Glu | Pro | Ile | Gln | Gly | Ala | Gly | Gly | Val | Ile | Val | Pro | Pro | Ala | Thr |
|---|---|---|---|---|---|---|---|---|---|---|---|---|---|---|---|
| 225 | | | | | 230 | | | | | 235 | | | | | 240 |

| Tyr | Trp | Pro | Glu | Ile | Glu | Arg | Ile | Cys | Arg | Lys | Tyr | Asp | Val | Leu | Leu |
|---|---|---|---|---|---|---|---|---|---|---|---|---|---|---|---|
| | | | | 245 | | | | | 250 | | | | | 255 | |

| Val | Ala | Asp | Glu | Val | Ile | Cys | Gly | Phe | Gly | Arg | Thr | Gly | Glu | Trp | Phe |
|---|---|---|---|---|---|---|---|---|---|---|---|---|---|---|---|
| | | | 260 | | | | | 265 | | | | | 270 | | |

| Gly | His | Gln | His | Phe | Gly | Phe | Gln | Pro | Asp | Leu | Phe | Thr | Ala | Ala | Lys |
|---|---|---|---|---|---|---|---|---|---|---|---|---|---|---|---|
| | | | 275 | | | | | 280 | | | | | 285 | | |

| Gly | Leu | Ser | Ser | Gly | Tyr | Leu | Pro | Ile | Gly | Ala | Val | Phe | Val | Gly | Asp |
|---|---|---|---|---|---|---|---|---|---|---|---|---|---|---|---|
| | 290 | | | | | 295 | | | | | 300 | | | | |

| Arg | Val | Ala | Glu | Gly | Leu | Ile | Ala | Gly | Gly | Asp | Phe | Asn | His | Gly | Phe |
|---|---|---|---|---|---|---|---|---|---|---|---|---|---|---|---|
| 305 | | | | | 310 | | | | | 315 | | | | | 320 |

| Thr | Tyr | Ser | Gly | His | Pro | Val | Cys | Ala | Ala | Val | Ala | His | Ala | Asn | Val |
|---|---|---|---|---|---|---|---|---|---|---|---|---|---|---|---|
| | | | | 325 | | | | | 330 | | | | | 335 | |

| Ala | Ala | Leu | Arg | Asp | Glu | Gly | Ile | Val | Gln | Arg | Val | Lys | Asp | Asp | Ile |
|---|---|---|---|---|---|---|---|---|---|---|---|---|---|---|---|
| | | | 340 | | | | | 345 | | | | | 350 | | |

| Gly | Pro | Tyr | Met | Gln | Lys | Arg | Trp | Arg | Glu | Thr | Phe | Ser | Arg | Phe | Glu |
|---|---|---|---|---|---|---|---|---|---|---|---|---|---|---|---|
| | | | 355 | | | | | 360 | | | | | 365 | | |

| His | Val | Asp | Asp | Val | Arg | Gly | Val | Gly | Met | Val | Leu | Ala | Phe | Thr | Leu |
|---|---|---|---|---|---|---|---|---|---|---|---|---|---|---|---|
| | 370 | | | | | 375 | | | | | 380 | | | | |

| Val | Lys | Asn | Lys | Ala | Lys | Arg | Glu | Leu | Phe | Pro | Asp | Phe | Gly | Glu | Ile |

```
        385                 390                 395                 400
Gly Thr Leu Cys Glu Asp Ile Phe Phe Arg Asn Gly Leu Ile Met Thr
                    405                 410                 415
Ala Cys Gly Asp His Ile Val Ser Ala Pro Pro Leu Val Met Thr Arg
                420                 425                 430
Ala Glu Val Asp Glu Met Leu Ala Val Ala Glu Arg Cys Leu Glu Glu
            435                 440                 445
Phe Glu Gln Thr Leu Lys Ala Arg Gly Leu Ala
        450                 455

<210> SEQ ID NO 48
<211> LENGTH: 459
<212> TYPE: PRT
<213> ORGANISM: Chromobacterium violaceum

<400> SEQUENCE: 48

Met Gln Lys Gln Arg Thr Cys Ser Gln Trp Arg Glu Leu Asp Ala Ala
1               5                   10                  15
His His Leu His Pro Phe Thr Asp Thr Ala Ser Leu Asn Gln Ala Gly
                20                  25                  30
Ala Arg Val Met Thr Arg Gly Glu Gly Val Tyr Leu Trp Asp Cys Glu
            35                  40                  45
Gly Asn Lys Ile Ile Asp Gly Met Ala Gly Leu Trp Cys Val Asn Val
        50                  55                  60
Gly Tyr Gly Arg Lys Asp Phe Ala Glu Ala Ala Arg Arg Gln Met Glu
65                  70                  75                  80
Glu Leu Pro Phe Tyr Asn Thr Phe Phe Gly Thr Thr His Pro Pro Val
                85                  90                  95
Val Glu Leu Ser Ser Leu Leu Ala Glu Val Thr Pro Ala Gly Phe Asp
                100                 105                 110
Arg Val Phe Tyr Thr Asn Ser Gly Ser Glu Ser Val Asp Thr Met Ile
            115                 120                 125
Arg Met Val Arg Arg Tyr Trp Asp Val Gln Gly Lys Pro Glu Lys Lys
        130                 135                 140
Thr Leu Ile Gly Arg Trp Asn Gly Tyr His Gly Ser Thr Ile Gly Gly
145                 150                 155                 160
Ala Ser Leu Gly Gly Met Lys Tyr Met His Glu Gln Gly Asp Leu Pro
                165                 170                 175
Ile Pro Gly Met Ala His Ile Glu Gln Pro Trp Trp Tyr Lys His Gly
                180                 185                 190
Lys Asp Met Thr Pro Asp Glu Phe Gly Val Val Ala Ala Arg Trp Leu
            195                 200                 205
Glu Glu Lys Ile Leu Glu Ile Gly Ala Asp Lys Val Ala Ala Phe Val
        210                 215                 220
Gly Glu Pro Ile Gln Gly Ala Gly Gly Val Ile Val Pro Pro Ala Thr
225                 230                 235                 240
Tyr Trp Pro Glu Ile Glu Arg Ile Cys Arg Lys Tyr Asp Val Leu Leu
                245                 250                 255
Val Ala Asp Glu Val Ile Cys Gly Phe Gly Arg Thr Gly Glu Trp Phe
                260                 265                 270
Gly His Gln His Phe Gly Phe Gln Pro Asp Leu Phe Thr Ala Ala Lys
            275                 280                 285
Gly Leu Ser Ser Gly Tyr Leu Pro Ile Gly Ala Val Phe Val Gly Asp
        290                 295                 300
```

-continued

```
Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Leu Ala Phe Thr Leu
            370                 375                 380

Val Lys Asn Lys Ala Lys Arg Glu Leu Phe Pro Asp Phe Gly Glu Ile
385                 390                 395                 400

Gly Pro Leu Cys Glu Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
450                 455

<210> SEQ ID NO 49
<211> LENGTH: 459
<212> TYPE: PRT
<213> ORGANISM: Chromobacterium violaceum

<400> SEQUENCE: 49

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Phe Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
        130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
            195                 200                 205

Glu Glu Lys Ile Leu Glu Ile Gly Ala Asp Lys Val Ala Ala Phe Val
        210                 215                 220
```

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
            245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Asp
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Leu Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 50
<211> LENGTH: 459
<212> TYPE: PRT
<213> ORGANISM: Chromobacterium violaceum

<400> SEQUENCE: 50

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
            85                  90                  95

Val Glu Leu Ser Ser Leu Leu Ala Glu Val Ala Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys 130                 135                 140
Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Asp
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Leu Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
450                 455

<210> SEQ ID NO 51
<211> LENGTH: 459
<212> TYPE: PRT
<213> ORGANISM: Chromobacterium violaceum

<400> SEQUENCE: 51

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Cys Glu
            35                  40                  45

```
Gly Asn Lys Ile Ile Asp Gly Met Ala Gly Leu Trp Cys Val Asn Val
 50                  55                  60
Gly Tyr Gly Arg Lys Asp Phe Ala Glu Ala Arg Arg Gln Met Glu
 65                  70                  75                  80
Glu Leu Pro Phe Tyr Asn Thr Phe Phe Gly Thr Thr His Pro Pro Val
                 85                  90                  95
Val Glu Leu Ser Ser Leu Leu Ala Glu Val Thr Pro Ala Pro Phe Asp
                100                 105                 110
Arg Val Phe Tyr Thr Asn Ser Gly Ser Glu Ser Val Asp Thr Met Ile
                115                 120                 125
Arg Met Val Arg Arg Tyr Trp Asp Val Gln Gly Lys Pro Glu Lys Lys
130                 135                 140
Thr Leu Ile Gly Arg Trp Asn Gly Tyr His Gly Ser Thr Ile Gly Gly
145                 150                 155                 160
Ala Ser Leu Gly Gly Met Lys Tyr Met His Glu Gln Gly Asp Leu Pro
                165                 170                 175
Ile Pro Gly Met Ala His Ile Glu Gln Pro Trp Trp Tyr Lys His Gly
                180                 185                 190
Lys Asp Met Thr Pro Asp Glu Phe Gly Val Val Ala Ala Arg Trp Leu
                195                 200                 205
Glu Glu Lys Ile Leu Glu Ile Gly Ala Asp Lys Val Ala Ala Phe Val
210                 215                 220
Gly Glu Pro Ile Gln Gly Ala Gly Gly Val Ile Val Pro Pro Ala Thr
225                 230                 235                 240
Tyr Trp Pro Glu Ile Glu Arg Ile Cys Arg Lys Tyr Asp Val Leu Leu
                245                 250                 255
Val Ala Asp Glu Val Ile Cys Gly Phe Gly Arg Thr Gly Glu Trp Phe
                260                 265                 270
Gly His Gln His Phe Gly Phe Gln Pro Asp Leu Phe Thr Ala Ala Lys
                275                 280                 285
Gly Leu Ser Ser Gly Tyr Leu Pro Ile Gly Ala Val Phe Val Gly Asp
                290                 295                 300
Arg Val Ala Glu Gly Leu Ile Ala Gly Gly Asp Phe Asn His Gly Phe
305                 310                 315                 320
Thr Tyr Ser Gly His Pro Val Cys Ala Ala Val Ala His Ala Asn Val
                325                 330                 335
Ala Ala Leu Arg Asp Glu Gly Ile Val Gln Arg Val Lys Asp Asp Ile
                340                 345                 350
Gly Pro Tyr Met Gln Lys Arg Trp Arg Glu Thr Phe Ser Arg Phe Glu
                355                 360                 365
His Val Asp Asp Val Arg Gly Val Gly Met Val Leu Ala Phe Thr Leu
                370                 375                 380
Val Lys Asn Lys Ala Lys Arg Glu Leu Phe Pro Asp Phe Gly Glu Ile
385                 390                 395                 400
Gly Thr Leu Cys Glu Asp Ile Phe Phe Arg Asn Asn Leu Ile Met Thr
                405                 410                 415
Ala Cys Gly Asp His Ile Val Ser Ala Pro Pro Leu Val Met Thr Arg
                420                 425                 430
Ala Glu Val Asp Glu Met Leu Ala Val Ala Glu Arg Cys Leu Glu Glu
                435                 440                 445
Phe Glu Gln Thr Leu Lys Ala Arg Gly Leu Ala
450                 455
```

```
<210> SEQ ID NO 52
<211> LENGTH: 459
<212> TYPE: PRT
<213> ORGANISM: Chromobacterium violaceum

<400> SEQUENCE: 52

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Leu Gly Ala Val Phe Val Gly Asp
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Leu Ala Phe Thr Leu
    370                 375                 380
```

```
Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
    450                 455

<210> SEQ ID NO 53
<211> LENGTH: 459
<212> TYPE: PRT
<213> ORGANISM: Chromobacterium violaceum

<400> SEQUENCE: 53

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Asn Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Ala Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Leu Gly Ala Val Phe Val Gly Asp
    290                 295                 300
```

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Pro
            355                 360                 365

His Val Asp Asp Val Arg Gly Val Gly Met Val Leu Ala Phe Thr Leu
        370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 54
<211> LENGTH: 459
<212> TYPE: PRT
<213> ORGANISM: Chromobacterium violaceum

<400> SEQUENCE: 54

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65              70                  75                  80

Glu Leu Pro Phe Tyr Asn Thr Phe Phe Gly Thr Thr His Pro Pro Val
            85                  90                  95

Val Glu Leu Ser Ser Leu Leu Ala Glu Val Ala Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
            165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val

```
                210                 215                 220
Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
                260                 265                 270

Gly His Gln His Phe Gly Phe Gln Pro Asp Leu Phe Thr Ala Ala Lys
                275                 280                 285

Gly Leu Ser Ser Gly Tyr Leu Pro Leu Gly Ala Val Phe Val Gly Asp
                290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
                340                 345                 350

Gly Pro Tyr Met Gln Lys Arg Trp Arg Glu Thr Phe Ser Arg Phe Pro
                355                 360                 365

His Val Asp Asp Val Arg Gly Val Gly Met Val Leu Ala Phe Thr Leu
                370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
                435                 440                 445

Phe Glu Gln Thr Leu Lys Ala Arg Gly Leu Ala
450                 455

<210> SEQ ID NO 55
<211> LENGTH: 459
<212> TYPE: PRT
<213> ORGANISM: Chromobacterium violaceum

<400> SEQUENCE: 55

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Cys Glu
                35                  40                  45

Gly Asn Lys Ile Ile Asp Gly Met Ala Gly Leu Trp Cys Val Asn Val
                50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Ala Pro Ala Gly Phe Asp
                100                 105                 110

Arg Val Phe Tyr Thr Asn Ser Gly Ser Glu Ser Val Asp Thr Met Ile
                115                 120                 125
```

```
Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Thr Ala Lys
        275                 280                 285

Gly Leu Ser Ser Gly Tyr Leu Pro Leu Gly Ala Val Phe Val Gly Asp
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Pro
        355                 360                 365

His Val Asp Asp Val Arg Gly Val Gly Met Val Leu Ala Phe Thr Leu
370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
450                 455
```

<210> SEQ ID NO 56
<211> LENGTH: 459
<212> TYPE: PRT
<213> ORGANISM: Chromobacterium violaceum

<400> SEQUENCE: 56

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45
```

```
Gly Asn Lys Ile Ile Asp Gly Met Ala Gly Leu Trp Cys Val Asn Val
 50                  55                  60

Gly Tyr Gly Arg Lys Asp Phe Ala Glu Ala Ala Arg Arg Gln Met Glu
 65                  70                  75                  80

Glu Leu Pro Phe Tyr Asn Thr Phe Phe Gly Thr Thr His Pro Pro Val
                     85                  90                  95

Val Glu Leu Ser Ser Leu Leu Ala Glu Val Ala Pro Ala Gly Phe Asp
                100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
                180                 185                 190

Lys Asp Met Thr Pro Asp Glu Phe Cys Val Val Ala Ala Arg Trp Leu
            195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Leu Gly Ala Val Phe Val Gly Asp
        290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Pro
        355                 360                 365

His Val Asp Asp Val Arg Gly Val Gly Met Val Leu Ala Phe Thr Leu
        370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
        450                 455
```

TRANSAMINASE MUTANT AND APPLICATION THEREOF

INCORPORATION BY REFERENCE

In compliance with 37 C.F.R. § 1.52(e)(5), M.P.E.P. § 608.05(I), the sequence information contained in electronic file name {SEQ_List_Final.txt}; created on Jul. 30, 2020 using Patent In 3.5.1, is hereby incorporated by reference in its entirety.

TECHNICAL FIELD

The invention relates to the field of enzyme engineering, in particular to a transaminase mutant and application thereof.

BACKGROUND

ω-transaminase (ω-TA) belongs to transferases and catalyzes the exchange of an amino group with a keto group like other transaminases. In most cases ω-transaminase refers to a class of enzyme, as long as the substrate or product of the reaction does not contain α-amino acid in an enzyme-catalyzed transamination reaction, the enzyme can be called ω-transaminase. ω-transaminases can efficiently produce chiral amines by stereoselective transamination using ketones as raw materials. Enantiomeric chiral amines are key intermediates for many pharmaceutical compounds with broad biological activity (*ChemBioChem.* 9, 2008, 363-365, *Chem. Commun.* 46, 2010, 5569-5571, *Biotechnol. Bioeng.* 108, 2011, 1479-1493). Because of the relatively cheap substrate and high purity of the product, it has attracted more and more attention from researchers (*Green Chemistry*, 2017, 19, 2: 333-360). And transaminases have shown promise for the production of chiral amines (*Organic Process Research & Development*, 2010, 14, 234-237).

Although much attention has been paid to the progress in producing chiral amines with transaminase, there are many problems in the application of enzymatic methods in scale-up production. For example, low enzyme activity and large amount of enzyme lead to the increase of fermentation cost, and are easy to be denatured and inactivated by the influence of organic solvents in the reaction system.

In addition, in the process of separating the product amine, the enzyme can only be denatured and inactivated to form precipitation and then removed and discarded, which cannot be reused, or the product is extracted from the aqueous solution with organic solvent, and the enzyme continues to exist in the aqueous solution, but at this time, due to the influence of many harsh conditions such as pH and solvent, the enzyme is inactivated and cannot be used again.

In the prior art, it has been reported that the enzyme is immobilized by immobilization technology to improve the recovery and reuse of the enzyme. However, at present, there are many researches on immobilization technology in the fields of lipase, penicillin acylase, amylase and others, because these enzymes have better stability than other enzymes, and the loss of enzyme activity after immobilization is lower. For most transaminases, the stability is poor, especially when an organic phase exists in the system, the loss of enzyme activity is easily to be caused in an immobilization operation process, so there is less research on the immobilization of transaminase and the research on immobilized transaminase suitable for continuous reaction is even less.

As for the transaminase capable of catalyzing the amino conversion reaction of the following substrate 1 and substrate 2, if the reaction is catalyzed by the free transaminase, the free enzyme cannot be recovered and can only be used once. In addition, due to the existence of enzyme protein in the reaction system, the post-treatment emulsification phenomenon is extremely serious, and the product separation is difficult.

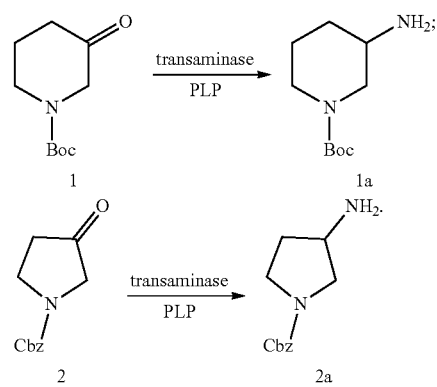

If the used transaminase is immobilized, the recovery and utilization of the enzyme can be realized theoretically, but the enzyme activity recovery is still low after the existing transaminase used for catalyzing the substrate 1 or the substrate 2 is immobilized. Moreover, since most of the existing substrate ketones (amino receptors) are poorly water-soluble, the continuous reaction cannot be carried out in a pure aqueous phase. In order to realize the continuous reaction, enough organic co-solvent needs to be added to dissolve the substrate, but the existing transaminase has poor tolerance to temperature, pH and organic solvent, and the organic solvent can easily inactivate the transaminase. It is thus difficult to realize its immobilization treatment.

Therefore, it is necessary to improve the existing transaminases which can catalyze the above substrates in order to improve their poor stability and limited application in extreme environments including organic solvents.

SUMMARY

The invention mainly aims to provide a transaminase mutant and application thereof, so as to solve the problem that the application is limited due to poor tolerance of the transaminase activity in an extreme environment in the prior art.

To achieve the above object, according to one aspect of the present invention, a transaminase mutant is provided, the transaminase mutant has a sequence in which an amino acid mutation occurs in the sequence shown in SEQ ID NO: 1, and sites of the amino acid mutation comprise T7C+S47C.

Further, the sites of the amino acid mutation further comprise any one or more of the following: M356L, F364L, C404L, M430L, R405E/A, K90G, K219T, K304D, K51R, A95P, E368P, Q346E, H333K, D371G, E246A, C328A, N412G, T402P, T107F/A, G110P, K69N, G201C, Q380L, K193I, I297L, R305H, F111Y, K190E and A286T, wherein "/" represents "or".

Further, the sites of the amino acid mutation further include any one of the following combined mutation sites: K51R+W187Y, R405E+A95P, R405E+A95P+K304D, R405E+A95P+K304D+Q380L, R405E+K90G+A95P+

K304D+Q380L, R405E+K90G+A95P+K304D+Q380L+ E368P, R405E+K90G+A95P+K304D+Q380L+Q346E, R405E+K90G+A95P+K304D+Q380L+H333K, R405E+ K90G+A95P+K304D+Q380L+D371G, R405E+K90G+ A95P+K304D+Q380L+E246A, R405E+K90G+A95P+ K304D+Q380L+C328A, R405E+K90G+A95P+K304D+ Q380L+N412G, R405E+K90G+A95P+K304D+Q380L+ T402P, R405E+K90G+A95P+K304D+Q380L+T107F, R405E+K90G+A95P+K304D+Q380L+T107A, R405E+ K90G+A95P+K304D+Q380L+G110P, R405E+K90G+ A95P+K304D+Q380L+I297L, R405E+K90G+A95P+ K304D+Q380L+I297L+E368P+T107A, R405E+K90G+ A95P+K304D+Q380L+I297L+A286T R405E+K90G+ A95P+K304D+Q380L+I297L+E368P R405E+K90G+ A95P+K304D+Q380L+I297L+E368P+T107A+K69N, R405E+K90G+A95P+K304D+Q380L+I297L+E368P+ T107A+G201C and R405E+K90G+A95P+K304D+ Q380L+I297L+E368P+T107A+A286T.

To achieve the above object, according to the second aspect of the present invention, a DNA molecule encoding any one of the transaminase mutants described above is provided.

According to the third aspect of the present invention, a recombinant plasmid having linked thereto any of the DNA molecules described above is provided.

According to the fourth aspect of the present invention, an immobilized transaminase comprising any one of the transaminase mutants described above is provided.

Further, the immobilized transaminase is a transaminase crosslinked enzyme aggregate of the transaminase mutant; preferably, the transaminase mutant is precipitated to obtain a transaminase aggregate, and a free amino, a phenolic, an imidazolyl, or a sulfhydryl group in the transaminase aggregate is further crosslinked with a cross-linking agent to obtain the transaminase cross-linked enzyme aggregate, wherein the cross-linking agent is selected from any one of glutaraldehyde, N, N-methylene bisacrylamide, bismaleimide and dextran; preferably, the transaminase cross-linked enzyme aggregate is a cross-linked enzyme aggregate of a transaminase mutant containing the following amino acid mutation sites on the basis of the amino acid sequence shown in SEQ ID NO:1: T7C+S47C, T7C+S47C+A95P, T7C+S47C+R405E+K90G+A95P+K304D+Q380L, T7C+ S47C+R405E+K90G+A95P+K304D+Q380L+I297L+ E368P+T107A, T7C+S47C+R405E+K90G+A95P+ K304D+Q380L+I297L+E368P+T107A+A286T, T7C+ S47C+R405E+K90G+A95P+K304D+Q380L+I297L+ E368P+T107A+K69N, T7C+S47C+R405E+K90G+A95P+ K304D+Q380L+H333K, T7C+S47C+R405E+K90G+ A95P+K304D+Q380L+E368P, T7C+S47C+K51R+ W187Y, T7C+S47C+R405E+K90G+A95P+K304D+ Q380L+Q346E, T7C+S47C+R405E+K90G+A95P+ K304D+Q380L+C328A and T7C+S47C+R405E+K90G+ A95P+K304D+Q380L+I297L; preferably, the dextran has a molecular weight of 6 KDa-200 KDa; preferably, the transaminase aggregate is obtained by ethanol precipitation of the transaminase mutant; preferably, a free amino group in the transaminase aggregate is cross-linked with glutaraldehyde to obtain transaminase cross-linked enzyme aggregates.

Further, the immobilized transaminase is a transaminase embedded-crosslinked immobilized enzyme; preferably, the transaminase embedded-crosslinked enzyme is an embedded-crosslinked immobilized enzyme of the transaminase mutant containing the following amino acid mutation sites on the basis of the amino acid sequence shown in SEQ ID NO: 1: T7C+S47C, T7C+S47C+R405E+K90G+A95P+ K304D+Q380L, T7C+S47C+R405E+K90G+A95P+ K304D+Q380L+I297L+E368P+T107A, T7C+S47C+ R405E+K90G+A95P+K304D+Q380L+Q346E and T7C+ S47C+R405E+K90G+A95P+K304D+Q380L+I297L; preferably, a free amino group in the transaminase mutant form a Schiff base by crosslinking with glutaraldehyde to obtain a transaminase cross-linked enzyme, and the transaminase cross-linked enzyme is embedded into a polyacrylamide gel grid to obtain the transaminase embedded-crosslinked immobilized enzyme.

Further, the immobilized transaminase is a covalent immobilized enzyme of which the transaminase mutant is covalently connected with the carrier; preferably, the covalently immobilized enzyme is a covalently immobilized enzyme of a transaminase mutant containing the following amino acid mutation site s on the basis of the amino acid sequence shown in SEQ ID NO:1: T7C+S47C, T7C+S47C+ A95P, T7C+S47C+Q380L, T7C+S47C+R405E, T7C+ S47C+K51R+W187Y, T7C+S47C+R405E+A95P+K304D, T7C+S47C+R405E+K90G+A95P+K304D+Q380L+E368P, T7C+S47C+R405E+K90G+A95P+K304D+Q380L, T7C+ S47C+R405E+K90G+A95P+K304D+Q380L+I297L, T7C+ S47C+R405E+K90G+A95P+K304D+Q380L+H333K, T7C+S47C+R405E+K90G+A95P+K304D+Q380L+ I297L+E368P+T107A and T7C+S47C+R405E+K90G+ A95P+K304D+Q380L+I297L+E368P+T107A+A286T; preferably, the carrier is a chitosan carrier and a resin carrier; more preferably, the chitosan carrier is covalently bound to the transaminase mutant by a hydroxyl and/or an amino group to form the covalent immobilized enzyme; more preferably, the resin carrier comprises a matrix and a functional group linked with the matrix, wherein the matrix is selected from any one of copolymers of styrene and methacrylate, polystyrene resins and polymethacrylate resins, and the functional group linked with the matrix is selected from a C2 short-chain amino group, a C4 medium-chain amino group, a C6 long-chain amino group or a epoxy group; further preferably, the resin carrier is selected from ECR8309, ECR8315, EC-HFA, LX-1000HA, LX-1000EA, ECR8409, ECR8415, EC-EP, ECEP403, EXE119, LX-1000EP, Immobead-150A, Immobead-150P, Immobead350A, ECR8206, ECR8209, ECR8215 or ECR8285.

Further, the immobilized transaminase is a chelating immobilized enzyme formed by chelating a transaminase mutant and a carrier through metal ions; preferably, the chelating immobilized enzyme is a chelating immobilized enzyme of a transaminase mutant containing the following amino acid mutation site s on the basis of the amino acid sequence shown in SEQ ID NO:1: T7C+S47C, T7C+S47C+ A95P, T7C+S47C+R405E+K90G+A95P+K304D+Q380L, T7C+S47C+R405E+K90G+A95P+K304D+Q380L+I297L, T7C+S47C+R405E+K90G+A95P+K304D+Q380L+ I297L+E368P+T107A+G201C and T7C+S47C+R405E+ K90G+A95P+K304D+Q380L+I297L+E368P+T107A+ A286T; preferably, the carrier is a porous glass carrier; further preferably, the porous glass carrier is EziG-101, EziG-102 or EziG-103.

Further, the immobilized transaminase is an adsorption immobilized enzyme formed by the transaminase mutant and the carrier through physical adsorption; preferably, the adsorption immobilized enzyme is a covalent immobilized enzyme of a transaminase mutant containing the following amino acid mutation site s on the basis of the amino acid sequence shown in SEQ ID NO:1: T7C+S47C, T7C+S47C+ A95P, T7C+S47C+R405E+K90G+A95P+K304D+Q380L+ I297L, T7C+S47C+R405E+K90G+A95P+K304D+Q380L+

H333K, T7C+S47C+R405E+K90G+A95P+K304D+Q380L+Q346E, T7C+S47C+R405E+K90G+A95P+K304D+Q380L+N412G, T7C+S47C+R405E+K90G+A95P+K304D+Q380L+I297L+E368P+T107A, T7C+S47C+R405E+K90G+A95P+K304D+Q380L+I297L+E368P+T107A+A286T and T7C+S47C+R405E+K90G+A95P+K304D+Q380L+I297L+E368P+T107A+G201C; preferably, the carrier is a resin carrier; more preferably, the resin carrier comprises a matrix and a functional group connected with the matrix, the matrix is selected from any one of a styrene and methacrylate copolymer, a polystyrene resin and a polymethacrylate resin, and the functional group connected with the matrix is an octadecyl; further preferably, the resin carrier is selected from ECR8806, ECR1030, ECR1090, ECR1061, ECR1091, ECR8804, Immobead-EC1, Immobead-5605, Immobead-5861, X1750409, EXE120 or Diaion HP2MG.

According to the fifth aspect of the present invention, a method for producing a chiral amine is provided, comprising the step of transamination reaction between a ketone compound and an amino donor catalyzed by a transaminase, wherein the transaminase is any one of the transaminase mutants above or any one of the immobilized transaminases above.

Further, the transaminase is any one of the transaminase mutants, and the method is a batch reaction; preferably, the reaction system of the batch reaction is an aqueous phase reaction system.

Further, the transaminase is any immobilized transaminase, and the method is a continuous reaction; preferably, the reaction system of the continuous reaction is an organic phase reaction system.

Further, the ketone compound is

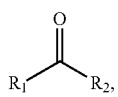

wherein R1 and R2 are each independently C1-C8 alkyl, C5-C10 cycloalkyl, C6-C10 aryl, or C5-C10 heteroaryl, or R1 and R2 together with the carbon on the carbonyl form a C5-C10 heterocyclyl, a C5-C10 carbocyclyl or a C5-C10 heteroaryl, the heteroatoms in the C5-C10 heterocyclyl and C5-C10 heteroaryl are each independently selected from at least one of nitrogen, oxygen and sulfur, the aryl in the C6-C10 aryl, the heteroaryl in the C5-C10 heteroaryl, the carbocyclyl in the C5-C10 carbocyclyl, or the heterocyclyl in the C5-C10 heterocyclyl is each independently unsubstituted or substituted with at least one of halogen, alkoxy or alkyl, preferably, the ketone compound is

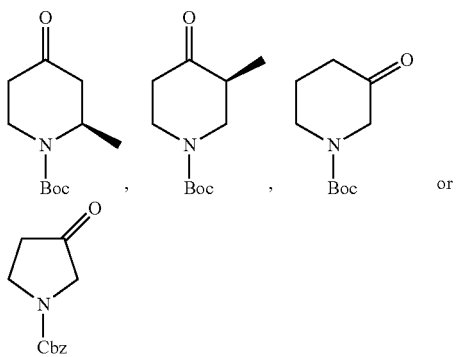

and the transamination reaction product is

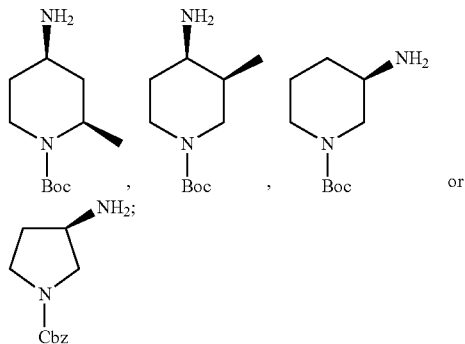

preferably, the amino donor is isopropyl amine.

According to the technical scheme provided by the invention, a series of transaminase mutants with greatly improved enzyme activity and/or stability are screened by performing directional evolution on the transaminase of the amino acid sequence shown in SEQ ID NO: 1, wherein the amino acid sequence of the mutants is an amino acid sequence which is mutated on the basis of the amino acid sequence shown in SEQ ID NO: 1, and the mutated amino acid sites comprise the T7C+S47C sites. The transaminase mutant containing the mutation sites above can be applied in a relatively extreme environment.

DETAILED DESCRIPTION OF THE INVENTION

It should be noted that the examples and features in the examples herein may be combined with one another without conflict. The present invention will be described in detail below in combination with the examples.

Term Explanation

Site-directed mutagenesis: refers to the introduction of desired changes (usually characterizing changes in favorable directions) to the target DNA fragments (either genomes or plasmids) by polymerase chain reaction (PCR), including addition, deletion, point mutation, etc. of bases. Site-directed mutagenesis can rapidly and efficiently improve the properties and characterization of target proteins expressed by DNA, and is a very useful means in gene research.

The introduction of site-directed mutation by whole plasmid PCR is simple and effective, and is a widely used method at present. The principle is as follows: a pair of primers containing mutation sites (forward and reverse), and the template plasmid is annealed, then "cycled extended" by polymerase, the so-called cyclic extension means that the polymerase extends the primers according to the template, and then returns to the 5' end of the primers after a circle, after cycles of repeated heating and annealing, this reaction is different from rolling circle amplification, will not form multiple tandem copies. The extension products of the forward primer and the reverse primer are annealed and paired to form a nicked open circular plasmid. Dpn I digests the extension product, since the original template plasmid is derived from conventional Escherichia coli (E. coli), subjected to dam methylation modification and sensitive to Dpn I, it is chopped, and the plasmid with the mutant sequence synthesized in vitro is not cut due to no methylation, so that the plasmid is successfully transformed in subsequent transformation, and clones of the mutant plasmid can be obtained. The mutant plasmid is transformed into a host cell to induce the target protein to be expressed.

Error-prone PCR: refers to the PCR under error-prone conditions, is a PCR technique that is easy to cause errors in copied DNA sequences, also known as mismatch PCR or error prone PCR. In particular, it refers to a method of inducing DNA sequence variation in vitro with low fidelity TaqDNA polymerase and changing PCR reaction conditions, reducing the fidelity of DNA replication and increasing base mismatch in the process of new DNA chain synthesis, resulting in more point mutations in the amplified products.

Error-prone PCR is the most simple and effective technique for gene random mutagenesis in vitro. Its principle is that base isomerization provides the possibility of mismatch. Tautomers are appeared in all the four bases that make up DNA, wherein three oxygen-containing base guanine (G), cytosine (C) and thymine (T), have two tautomers of keto form and enol form. The two nitrogen-containing bases, adenine (A) and thymine, have an amine form and an imine form. G, C and T exist mainly in a keto form structure, the ratio of the enol form structure is extremely low, and the nitrogen atoms on the nitrogen-containing bases A and T mainly exist in an amino ($NH_2$) state, and the ratio of the nitrogen atoms in the imine (NH) state is extremely low. The different positions of hydrogen atoms between different isomers and the different deviation directions of electron clouds at the same position can change the pairing forms of bases, so that mismatches can occur on the replicated sub-chains. For example, when thymine is present in a keto form structure, paired with adenine, and when thymine in an enol form structure, paired with guanine, thus giving rise to an unstable base pair in which A can be matched with C and T can be matched with G, resulting in a mismatch.

Among several known thermo-tolerance DNA polymerases, TaqDNA polymerase has the highest mismatch rate. TaqDNA polymerase has the highest activity among the found thermo-tolerance DNA polymerases. It has 5'-3' exonuclease activity, but not 3'-5' exonuclease activity, therefore, it has no correction function for some mononucleotide mismatches during synthesis, so it has a higher probability of mismatch than DNA polymerases with 3'-5' correcting activity. The fidelity of DNA polymerases can be reduced by a variety of methods, including using four dNTPs of different concentrations, adding $Mn^{2+}$, increasing $Mg^{2+}$ concentration, etc. Several mutagenesis methods lead to different mechanisms of base variation in amplified DNA chain. $MnCl_2$ is a mutagenic factor of DNA polymerases, adding $Mn^{2+}$ can reduce the specificity of polymerase to template and improve the mismatch rate; the unbalance of the concentrations of the four dNTPs can improve the probability of base misincorporation and realize mismatch; $Mg^{2+}$ has the function of activating Taq enzyme, increasing the concentration of $Mg^{2+}$ to exceed the normal dosage can stabilize the non-complementary base pairs; increasing the dosage of TaqDNA polymerase and the extension time of each cycle can increase the probability of mismatch terminal extension; decreasing the initial template concentration will increase the proportion of variant templates in the following PCR cycle.

Immobilized enzyme: refers to an enzyme whose catalysis can be repeatedly and continuously used within a certain space range. Generally, enzyme catalyzed reaction is carried out in aqueous solutions, whereas immobilized enzymes are physically or chemically treated to render water-soluble enzymes insoluble but still enzymatically active. After immobilization, the general stability of enzyme is increased, it is easy to separate from the reaction system, easy to control, can be used many times, easy to transport and store and is favorable to automatic production, but the activity and the use range is reduced.

Immobilized enzyme carrier matrix: refers to a material that forms the backbone of an immobilized enzyme carrier.

As used herein, 1 wt refers to 1 g of transaminase mutant recombinant wet cells required to transform 1 g of substrate.

In the present application, the 1V referred to is equal to the volume of the reaction system/mass of the substrate.

In order to solve the problem that the application is limited due to poor tolerance of transaminase activity in an extreme environment in the prior art, a typical embodiment of the application carries out directed evolution on the transaminase which is mutated at the R416T site from the *Chromobacterium violaceum* to obtain the transaminase mutant, wherein the transaminase mutant has a sequence in which an amino acid mutation occurs in the sequence shown in SEQ ID NO: 1; the site at which the amino acid mutation occurs includes the T7C+S47C site. In the relatively extreme environment, the mutational transaminase activity of the transaminase with mutation occurs at R416T+T7C+S47C site was significantly higher than that of the R416T mutant.

Hereinafter, the above technical solutions and effects will be described with reference to experiments.

I. Screening of Mutants with Improved Tolerance to Extreme Environments

The transaminase derived from the *Chromobacterium violaceum* was modified in the present invention to obtain the R416T mutant with improved enzyme activity, and the amino acid sequence of the R416T mutant is shown in SEQ ID NO: 1. The activity of the enzyme is good, but its stability is not ideal. In order to improve the stability of the enzyme, five groups of double-point mutations Q78C+A330C, V137C+G313C, A217C+Y252C, T7C+S47C and L295C+328C were designed with the R416T mutant as the template, and a primer sequence was designed with a QuikChange Primer Design webpage. The mutant site was introduced into the mutant R416T by whole plasmid PCR, and the mutant plasmid with new mutation site was obtained with pET-22b(+) as the expression vector.

The mutant plasmid was transformed into *E. coli* cells and induced overnight under the optimal conditions of transaminase-induced expression at 25° C. and 0.1 mM IPTG, and then the crude enzyme was obtained by ultrasonication of the cells. After the enzyme solution expressed by the mutant strain was treated for 1 h in the extreme environment of 45-50° C., pH 9.5 and 20% DMSO, substrate 1 or substrate 2 was added, and the enzyme amount of 1 wt was used to continue to react under this condition for 16 h, and then the transformation rate was detected. The mutant with improved stability was screened by this method, in which the activity of the mutant (R416T+T7C+S47C) at T7C+S47C sites was significantly higher than that of the R416T mutant. Under this condition, the transformation rate catalyzed by R416T was 15%, while that catalyzed by mutant R416T+T7C+S47C was 72%.

Furthermore, using the R416T+T7C+S47C mutant as the female parent, 33 pairs of site-directed mutagenesis (specific primers designed by QuikChange Primer Design web page) (M356L, w360L, F364L, C404L, M430L, M438L, C445A, F449V, R405E, R405A, K90G, K190R, K219T, K304D, K51R, W187Y, K193E, K143R, N151M, S8P, A33P, A95P, E368P, Q346E, H333K, D371G, E246A, C328A, N412G, T402P, T107F, T107A, G110P), the primer sequences were designed by QuikChange Primer Design web page, and the mutant plasmid with target gene was obtained by site-directed mutagenesis with pET-22b (+) as expression vector. The mutant plasmid was transformed into E. coli cells and induced overnight under the optimal conditions of transaminase-induced expression at 25° C. and 0.1 mM IPTG. Then the crude enzyme was obtained by ultrasonication of the cells.

After the enzyme solution expressed by the mutant strain was treated for 1 h in the extreme environment of 30-45° C., pH 9.5-10 and 50% DMSO, substrate 1 or substrate 2 was added, and continued to react under this condition for 16 h, and then the transformation rate was detected. Mutants with enhanced tolerance to temperature, pH and organic solvent were screened in this manner. The screen results are: the tolerance of the mutant with mutation site at M356L, F364L, C404L, M430L, R405E, R405A, K90G, K219T, K304D, K51R, A95P, E368P, Q346E, H333K, D371G, E246A, C328A, N412G, T402P, T107F, T107A, G110P to the environment of 30° C., pH9.5 and 50% DMSO was 8%-40% higher than that of R416T+T7C+S47C mutant. The tolerance of some mutants to the environment of 45° C., pH 9.5, 50% DMSO was 1.7-2.1 times higher than that of R416T+T7C+S47C mutant, and the tolerance of some mutants to the environment of 40° C., pH 10, 50% DMSO was 3.7-3.9 times higher than that of R416T+T7C+S47C mutant.

With the R416T+T7C+S47C mutant as the female parent, specific mutants with improved tolerance under different extreme environments were screened by site-directed mutagenesis as shown in Table 1 and Table 2 below.

TABLE 1 single point mutants with improved tolerance to the environment of 30° C., pH 9.5, 50% DMSO obtained by site-directed mutagenesis.

| Mutation site | Degree of tolerance improvement | Mutation site | Degree of tolerance improvement | Mutation site | Degree of tolerance improvement |
| --- | --- | --- | --- | --- | --- |
| Female parent R416T + T7C + S47C | No | D371G | 23% | T107F | 36% |
| K90G | 8% | T402P | 25% | E368P | 43% |
| K219T | 9% | R405A | 27% | C328A | 39% |
| M430L | 13% | E246A | 29% | T107A | 39% |
| K51R | 14% | H333K | 30% | R405E | 41% |
| C404L | 16% | A95P | 31% | N412G | 19% |
| M356L | 18% | G110P | 32% | Q346E | 35% |
| F364L | 18% | K304D | 34% | –/– | –/– |

TABLE 2 single point mutants with improved tolerance to the environment of 40° C., pH 10, 50% DMSO obtained by site-directed mutagenesis.

| Mutation site | Degree of tolerance improvement | Mutation site | Degree of tolerance improvement | Mutation site | Degree of tolerance improvement |
| --- | --- | --- | --- | --- | --- |
| R416T + T7C + S47C | No | C328A | 312% | A95P | 387% |
| G110P | 98% | D371G | 286% | Q346E | 409% |
| H333K | 377% | T402P | 326% | E368P | 421% |
| T107A | 342% | T107F | 339% | R405E | 369% |
| E246A | 253% | –/– | –/– | –/– | –/– |

In order to simply and effectively screen more ideal mutants, the R416T+T7C+S47C mutant is randomly mutated by adopting an error-prone PCR technology in the present invention.

In this application, the target gene fragment was linked to the pET-22b vector by error-prone PCR method, and mutant plasmid with the target gene was obtained. The mutant plasmid was transformed into *E. coli* cells and induced overnight under the optimal conditions of transaminase-induced expression at 25° C. and 0.1 mM IPTG. Finally, the crude enzyme was obtained by ultrasonication of the cells.

After the enzyme solution expressed by the mutant strain was treated for 1 h in the extreme environment of 30-45° C., pH9-10 and an organic solvent concentration of 50% DMSO or 35% MeOH, substrate 1 or substrate 2 was added, and continued to react under this condition for 16 h, then the transformation rate was detected. Mutants with enhanced tolerance to temperature, pH and organic solvents were screened in this manner. The screen results showed that the tolerance of the mutant with mutation site at K69N, G201C, Q380L, K193I, I297L, R305H, F111Y, K190E, A286T to the environment of 30° C., pH 9.5 and 50% DMSO was 16%-45% higher than that of R416T+T7C+S47C mutant. The tolerance of some mutants to the environment of 40° C., pH 10, 50% DMSO was 117%-537% higher than that of R416T+T7C+S47C mutant, and the tolerance of some mutants to the environment of 30° C., pH 8, 35% MeOH was 233%-649% higher than that of female parent.

With the R416T+T7C+S47C mutant as the female parent, specific mutants with improved tolerance under different extreme environments were screened by error-prone PCR as shown in Table 3 to Table 5 below.

TABLE 3 single point mutants with improved tolerance to the environment of 30° C., pH 9.5, 50% DMSO obtained by error-prone PCR.

| Mutation site | Degree of tolerance improvement | Mutation site | Degree of tolerance improvement |
|---|---|---|---|
| R416T + T7C + S47C | No | K193I | 38% |
| F111Y | 16% | K190E | 31% |
| Q380L | 41% | R305H | 43% |
| I297L | 42% | A286T | 45% |
| K69N | 24% | G201C | 28% |

TABLE 4 single point mutants with improved tolerance to the environment of 40° C., pH 10, 50% DMSO obtained by error-prone PCR.

| Mutation site | Degree of tolerance improvement | Mutation site | Degree of tolerance improvement |
|---|---|---|---|
| R416T + T7C + S47C | No | Q380L | 509% |
| K190E | 191% | K193I | 312% |
| F111Y | 238% | I297L | 537% |
| R305H | 174% | K190E | 191% |
| K69N | 124% | G201C | 117% |

TABLE 5 single point mutants with improved tolerance to the environment of 30° C., pH 8, 35% MeOH obtained by error-prone PCR

| Mutation site | Degree of tolerance improvement | Mutation site | Degree of tolerance improvement |
|---|---|---|---|
| R416T + T7C + S47C | No | R305H | 497% |
| F111Y | 233% | I297L | 576% |
| K190E | 403% | K193I | 579% |
| A286T | 623% | Q380L | 649% |
| K69N | 288% | G201C | 294% |

In order to further evolve transaminases with better stability and tolerance, in the present invention, the sites with improved stability and tolerance of the transaminases are subjected to multi-point combined mutation, and then the multi-point mutants with further improved stability and tolerance are obtained by a directed screening method.

Mutation sites for combined mutations were from K51R, W187Y, R405E, K90G, A95P, K304D, Q380L, E368P, Q346E, H333K, D371G, E246A, C328A, N412G, T402P, T107F, T107A, G110P, I297L, K69N, G201C and A286T.

The combined mutation is any combination of these sites. In particular, the combined mutation include, but are not limited to the following: K51R+W187Y, R405E+A95P, R405E+A95P+K304D, R405E+A95P+K304D+Q380L, R405E+K90G+A95P+K304D+Q380L, R405E+K90G+A95P+K304D+Q380L+E368P, R405E+K90G+A95P+K304D+Q380L+Q346E, R405E+K90G+A95P+K304D+Q380L+H333K, R405E+K90G+A95P+K304D+Q380L+D371G, R405E+K90G+A95P+K304D+Q380L+E246A, R405E+K90G+A95P+K304D+Q380L+C328A, R405E+K90G+A95P+K304D+Q380L+N412G, R405E+K90G+A95P+K304D+Q380L+T402P, R405E+K90G+A95P+K304D+Q380L+T107F, R405E+K90G+A95P+K304D+Q380L+T107A, R405E+K90G+A95P+K304D+Q380L+G110P, R405E+K90G+A95P+K304D+Q380L+I297L, R405E+K90G+A95P+K304D+Q380L+I297L+E368P+T107A, R405E+K90G+A95P+K304D+Q380L+I297L+A286T, R405E+K90G+A95P+K304D+Q380L+I297L+E368P, R405E+K90G+A95P+K304D+Q380L+I297L+E368P+T107A+K69N, R405E+K90G+A95P+K304D+Q380L+I297L+E368P+T107A+G201C and R405E+K90G+A95P+K304D+Q380L+I297L+E368P+T107A+A286T.

The mutant plasmid was transformed into *E. coli* cells and induced overnight under the optimal conditions of transaminase-induced expression at 25° C. and 0.1 mM IPTG. Then the crude enzyme was obtained by ultrasonication of the cells.

After the enzyme solution was treated for 1 h in more extreme environment of 45° C., pH 9.5-10 and containing 50% DMSO or 35% MeOH, substrate 1 was added, and continued to react under this condition for 16 h, then the transformation rate was detected. The tolerance of some combined mutants to the environment of 40° C., pH 10, 50% DMSO was 231%-610% higher than that of the female parent, the tolerance of some combined mutants to the environment of 30° C., pH 8, 35% MeOH was 213%-990% higher than that of the female parent, and the tolerance of some combined mutants to the environment of 45° C., pH 8, 40% MeOH was 3000% higher than that of the female parent. Specific combined mutants with improved tolerance are shown in Tables 6 to 8 below.

TABLE 6 combined mutants with improved tolerance to the environment of 40° C., pH 10, 50% DMSO.

| Mutation site | Degree of tolerance improvement | Mutation site | Degree of tolerance improvement |
|---|---|---|---|
| R416T + T7C + S47C | No | R405E + A95P | 231% |
| K51R + W187Y | 507% | R405E + K90G + A95P + K304D + Q380L + E246A | 298% |
| R405E + A95P + K304D | 572% | R405E + K90G + A95P + K304D + Q380L + C328A | 334% |
| R405E + A95P + K304D + Q380L | 562% | R405E + K90G + A95P + K304D + Q380L + N412G | 246% |
| R405E + K90G + A95P + K304D + Q380L | 586% | R405E + K90G + A95P + K304D + Q380L + T402P | 323% |
| R405E + K90G + A95P + K304D + Q380L + E368P | 611% | R405E + K90G + A95P + K304D + Q380L + T107F | 498% |
| R405E + K90G + A95P + K304D + Q380L + Q346E | 552% | R405E + K90G + A95P + K304D + Q380L + T107A | 573% |
| R405E + K90G + A95P + K304D + Q380L + H333K | 563% | R405E + K90G + A95P + K304D + Q380L + G110P | 317% |
| R405E + K90G + A95P + K304D + Q380L + D371G | 368% | R405E + K90G + A95P + K304D + Q380L + I297L | 610% |

TABLE 7 combined mutants with improved tolerance to the environment of 30° C., pH 8, 35% MeOH.

| Mutation site | Degree of tolerance improvement | Mutation site | Degree of tolerance improvement |
|---|---|---|---|
| R416T + T7C + S47C | No | R405E + K90G + A95P + K304D + Q380L + C328A | 783% |
| R405E + K90G + A95P + K304D + Q380L + D371G | 213% | R405E + K90G + A95P + K304D + Q380L + T107A | 837% |
| R405E + K90G + A95P + K304D + Q380L + T402P | 288% | K51R + W187Y | 866% |
| R405E + K90G + A95P + K304D + Q380L + N412G | 354% | R405E + K90G + A95P + K304D + Q380L + E368P | 925% |
| R405E + K90G + A95P + K304D + Q380L | 557% | R405E + K90G + A95P + K304D + Q380L + I297L + E368P + T107A | 979% |
| R405E + K90G + A95P + K304D + Q380L + Q346E | 773% | R405E + K90G + A95P + K304D + Q380L + I297L | 990% |
| R405E + K90G + A95P + K304D + Q380L + H333K | 783% | R405E + K90G + A95P + K304D + Q380L + I297L + E368P + T107A + A286T | 697% |
| R405E + K90G + A95P + K304D + Q380L + I297L + E368P + T107A + K69N | 596% | R405E + K90G + A95P + K304D + Q380L + I297L + E368P + T107A + G201C | 623% |

TABLE 8 combined mutants with increased tolerance to the environment of 45° C., pH 8, 40% MeOH.

| Mutation site | Degree of tolerance improvement | Mutation site | Degree of tolerance improvement |
|---|---|---|---|
| R416T + T7C + S47C | No | R405E + K90G + A95P + K304D + Q380L + I297L + A286T | 3090% |
| R405E + K90G + A95P + K304D + Q380L + I297L | 3100% | R405E + K90G + A95P + K304D + Q380L + I297L + E368P | 3000% |
| R405E + K90G + A95P + K304D + Q380L + I297L + E368P + T107A + K69N | 2889% | R405E + K90G + A95P + K304D + Q380L + I297L + E368P + T107A + G201C | 2927% |
| R405E + K90G + A95P + K304D + Q380L + I297L + E368P + T107A | 3010% | R405E + K90G + A95P + K304D + Q380L + I297L + E368P + T107A + A286T | 2996% |

II. Immobilizing the Transaminase Mutant of the Application 2.1 Preparation of Transaminase Cross-Linked Enzyme Aggregates (CLEAs)

In the application, transaminases of female parent R416T+T7C+S47C mutant, single point mutants and combined mutants screened on the basis of female parent mutant were immobilized by cross-linking method to prepare transaminase cross-linked enzyme aggregates.

In general, the preparation of the cross-linked enzyme aggregates is mainly carried out in two steps: (1) forming an enzyme protein aggregation precipitate; (2) cross-linking between precipitates.

The enzyme protein can be coagulated and precipitated by a salt fractionation, an isoelectric precipitation method, a heavy metal salt precipitation method or an organic solvent precipitation method to obtain enzyme protein aggregates. Typically, the enzymatic protein precipitate is a reversible precipitate that can be re-dissolved in aqueous solution.

And after protein precipitation, adding a cross-linking agent to further connect protein precipitates through covalent bonds to form water-insoluble precipitate-cross-linked enzyme aggregates. The cross-linking agent used is a bifunctional or multifunctional reagent, the bifunctional reagent comprises glutaraldehyde, N, N-methylene bisacrylamide (MBA), bismaleimide and the like, and the multifunctional reagent dextran (molecular weight is 6 KDa-200 KDa). Free amino group, phenol group, imidazole group and sulfhydryl group of enzyme protein can participate in cross-linking reaction.

The buffer for preparing the immobilized enzyme solution contains PLP of 0.4-1 mg/mL, and the pH value of the enzyme solution is 7.0-8.0. The precipitant used for preparing the enzyme protein precipitate is ethanol, isopropanol and/or ammonium sulfate, and the final concentration of the precipitant is 90%. The cross-linking agent used to prepare the cross-linked aggregates of the enzyme proteins was a 25% glutaraldehyde solution with a final glutaraldehyde concentration of 200 mM-500 mM.

The prepared cross-linked enzyme aggregate can be directly subjected to catalytic reaction in an aqueous phase with the aqueous cross-linked enzyme obtained by filtration, or the aqueous cross-linked enzyme can be lyophilized to obtain a dry powder and then applied. The lyophilized powder may also be applied to the reaction in the organic solvent phase. After the cross-linked enzyme aggregate is used once, the cross-linked enzyme aggregate can be recovered by centrifuging or filtering and the like and then used again, the repeated use times are counted in the range that the activity loss is less than 5% compared with the first use, the cross-linked enzyme aggregate is used in an aqueous phase. Compared with the free enzyme, the activity recovery is more than 80%, and the female parent R416T+T7C+S47C can be reused for 3 times, the reuse times of single point mutants and/or combined mutants on the basis of female parent were significantly higher than those of female parents, and the reuse times of the best mutants were up to 13 times.

The cross-linked enzymes of some mutants can be reused at least 6 times in a system containing 35% methanol. The stability of free enzyme activity of the mutant was improved, and the enzyme activity recovery and reuse times were also increased after immobilization.

The emulsification phenomenon was obviously reduced with cross-linked enzyme to catalyze the reaction and extracting the product from the aqueous phase with organic solvent after the reaction. The preparation of cross-linked enzyme has the advantages of no carrier, low cost, catalyzing reaction with cross-linked enzyme, more times of repeated use, comprehensive use times, reduced amount of enzyme and lower cost than free enzyme. The cross-linked enzyme lyophilized powder is reacted in 100% organic phase solvent, and when the female parent is repeatedly used for the second time, the activity is lost by more than 10% compared with that for the first time. However, some mutants could be reused up to 5 times with less than 5% loss of activity compared to the first time.

2.2 Embedded-Crosslinked Immobilization Method of Transaminase

CLEAs have no carrier support, small immobilized enzyme particles (<10 pin) and poor mechanical strength, the enzyme is easy to harden in the process of filtering and recovering the enzyme, and the enzyme cannot be well dispersed in the reaction system in the next use.

In order to solve the problem, glutaraldehyde can be used as a cross-linking agent in combination with two technologies of cross-linking and embedding, glutaraldehyde is added dropwise to a mixed solution containing enzyme liquid, acrylamide and methylene diacrylamide to enable the glutaraldehyde and free enzyme to form Schiff base to prepare a cross-linked enzyme aggregate, an initiator ammonium persulfate is added to form polyacrylamide gel, and the cross-linked enzyme aggregate is embedded into a polyacrylamide gel matrix to obtain stable immobilized enzyme.

In the application, transaminases of female parent R416T+T7C+S47C mutant, single point mutants and combined mutants screened on the basis of female parent mutant were immobilized by embedded-crosslinked method to prepare embedded-crosslinked enzyme.

The prepared embedded-crosslinked enzyme, whose enzyme activity recovery is more than 80%, after the aqueous phase reaction is used once, it can be easily recovered by filtering and the like and then used again, the repeated use times are counted in the range that the activity loss is less than 5% compared with the first use, the female parent R416T+T7C+S47C can be reused for 8 times, the reuse times of single point mutants and/or combined mutants on the basis of female parents were significantly higher than those of female parents, and the reuse times of the best mutants were up to 18 times.

The embedded-crosslinked enzymes of some mutants can be reused at least 12 times in a system containing 35% methanol. Extracting the product from the aqueous phase with organic solvent after the reaction, the emulsification phenomenon was obviously reduced.

2.3 Adsorption Immobilization Method of Transaminase

The adsorbed immobilized enzyme can be prepared by the adsorption and combination of enzyme molecule and water-insoluble carrier by means of electrostatic interaction, hydrogen bond, hydrophobic interaction and so on. The method has mild conditions and is not easy to cause denaturation of the enzyme, but the enzyme is easily separated from the carrier in aqueous solution and cannot be recycled, so the immobilized enzyme prepared by adsorption method is mainly used in the reaction in organic solvents.

The carriers that can be used to adsorbed immobilized enzymes can be divided into two types: inorganic carriers and macromolecular carrier. Inorganic carriers include activated carbon, porous glass, emathlite, bleaching clay, kaolinite, alumina, silica gel, bentonite, hydroxyapatite, calcium phosphate, metal oxides and the like; macromolecular carriers include starch, glutelin, macroporous synthetic resins, ceramics, etc.

The carrier used in the application is a macroporous synthetic resin carrier, comprising a matrix and an optional functional group that modify the matrix, wherein the matrix includes, but is not limited to, polystyrene resin, polymethacrylate resin or styrene-methacrylate copolymer. In addition, various types of carriers can be modified with octadecyl functional group. Table 9 below is listed as the carrier suitable for the adsorption and immobilization of transaminase in the application.

TABLE 9

| Adsorption type carrier | | |
| --- | --- | --- |
| Carrier Name | Matrix | Functional Group |
| Diaion | Polymethacrylate | No |
| X17S0401 | Polymethacrylate | No |
| ECR8806 | Polymethacrylate | No |
| EXE120 | Polymethacrylate | Octadecyl |
| ECR-1030 | Polymethacrylate | No |
| ECR-1090 | polystyrene | No |

In this application, the transaminase and the macroporous resin carrier are directly combined in physical modes such as hydrophobic bonds, hydrogen bonds and the like.

Transaminases of female parent R416T+T7C+S47C mutant, single point mutants and combined mutants screened on the basis of female parent mutant were immobilized by physical adsorption binding method.

The buffer used for preparing the enzyme solution contains 0.4-1 mg/mL of PLP, the pH of the buffer is 7.0-8.0, and the buffer salt is $Na_2HPO_4$—$NaH_2PO_4$, Tris-Cl or boric acid-sodium hydroxide.

The prepared adsorption immobilized enzyme can be dried by nitrogen blow drying, vacuum drying, freeze drying and so on.

In this application, the transaminase is bound to the carrier by adsorption, and the activity recovery is more than 80%; reacting in organic solvent, the immobilized enzyme is recovered by filtration or liquid suction by syringe, which can be reused. Compared with the first use, the number of repeated uses was counted in the range of activity loss less than 5%. For some mutant immobilized enzymes, the immobilized enzyme could be reused for 6 times, and the activity loss was less than 5%.

2.4 Covalent Immobilization Method of Transaminase

Covalent immobilization of an enzyme is that a non-essential group of an enzyme protein is irreversibly linked with a water-insoluble carrier through a covalent bond, and protein groups capable of being coupled under mild conditions comprise: amino, carboxyl, sulfhydryl of cysteine, imidazolyl of histidine, phenolic group of tyrosine, hydroxyl of serine and threonine. The group covalently bound with the carrier is usually not the group necessary for the enzyme to express activity.

2.4.1 Covalent Immobilized Enzyme Carrier

The immobilized enzyme carrier can be inorganic materials such as silica, glass, minerals, celite and the like; natural organic materials such as carboxymethyl cellulose, dextran, agarose, pectin, chitosan and the like; and non-natural organic synthetic polymers such as polystyrene resins, polymethacrylate resins or copolymers of styrene and methacrylate. These carriers may be further functionalized to facilitate binding to the protein molecule, such as by incorporating amino, hydroxyl, epoxy, octadecyl and other functional groups on the carrier. The amino-functional carrier and the hydroxyl-functional carrier can bind to enzyme protein molecule through ionic bonds, the amino-type carrier can also covalently bind to the enzyme protein, the epoxy-functional carrier mainly binds to the enzyme protein through covalent bonds, and the octadecyl-functional carrier binds to the enzyme molecule through hydrophobic interaction. The carrier may take any shape or form, such as a film, tube, sheet, bead, particle, chip, optical fiber, etc.

The carrier used in the present application is chitosan, resin and porous glass.

Chitosan can be used as a carrier for enzyme immobilization because of its good biocompatibility, high shape plasticity (which can be made into gel, film, fiber and other shapes), non-toxicity, easy chemical modification and other characteristics (*ProcessBiochem*, 2005; 40: 2833-40). Chitosan itself is soluble in water and needs to be prepared into water-insoluble carrier particles by solvent evaporation, emulsification, coacervation and other methods (*MacromolBiosci*, 2003; 3: 511-20). The carrier particles produced by emulsification are small and uniform and are generally preferred. The chitosan molecules have active hydroxyl groups, amino groups and the like, the enzyme can be adsorbed and bound through ionic bonds, hydrogen bonds, Van der Waals force and others, but the adsorption effect is weak, the enzyme is easy to fall off, and the common cross-linking agents such as formaldehyde, glutaraldehyde and the like are activated and then covalently bound to the enzyme.

The resin carrier used in the application comprises a matrix and functional groups that modify the matrix, wherein the matrix includes, but is not limited to, polystyrene resins, polymethacrylate resins and copolymers of styrene-methacrylate. Suitable functional groups carried by such matrixs include, but are not limited to, short-chain amino groups, long-chain amino groups and epoxy groups. Table 10 below is listed as the carrier suitable for the immobilization of transaminase in the application.

TABLE 10

| Carrier Name | Matrix | Functional Group |
|---|---|---|
| ECR8309 | Polymethacrylate | Short-chain amino group (C2) |
| ECR8409 | Polymethacrylate | Long-chain amino group (C6) |
| ECR8285 | Polymethacrylate | Epoxy-group |

In the application, the transaminase is directly bound to the resin with epoxy functional group through covalent bond, and to the resin with amino functional group activated by glutaraldehyde through covalent bond.

2.4.2 Method of Covalent Immobilization

In the application, transaminases of female parent R416T+T7C+S47C mutant, single point mutants and combined mutants screened on the basis of female parent mutant were immobilized by covalent binding method.

The buffer solution used for preparing the enzyme solution contains 0.4-1 mg/mL of PLP, the pH of the buffer solution is 7.0-8.0, and the buffer salt is $Na_2HPO_4$—$NaH_2PO_4$, Tris-Cl or boric acid-sodium hydroxide. The molecular weight of chitosan used in the present application includes, but is not limited to, 300-500 KDa, a carrier is prepared by an emulsification method, after activating the carrier with glutaraldehyde, adding enzyme solution, incubating for 6 h at 20° C., collecting the precipitate by filtration or centrifugation, and rinsing the precipitate with buffer.

Covalently immobilized to the amino-type carrier, first activating the carrier with glutaraldehyde, then adding enzyme solution, incubating overnight at 20° C., collecting the precipitate by filtration, and rinsing the precipitate with buffer. Covalently immobilized to epoxy-based carrier, directly mixing enzyme solution with the carrier, incubating overnight at 20° C., then standing for 20 h, collecting the precipitate by filtration, and rinsing the precipitate with buffer.

The prepared immobilized enzyme can be dried by nitrogen blow drying, vacuum drying, freeze drying and so on.

In the application, the transaminase is immobilized to the above carriers by covalent binding, and immobilized to a chitosan carrier, and the activity recovery is 50%-60%; immobilized to a short-chain amino carrier, the activity recovery is 50%-70%; immobilized to a long-chain amino-type carrier, the activity recovery is 70%-80%; immobilized to an epoxy-based carrier, the activity recovery is 40%-60%. The activity of the immobilized enzyme of the mutant is obviously improved compared with that of the female parent immobilized enzyme. The immobilized enzyme is recovered by filtration or liquid suction by syringe, which can be reused. Compared with the first use, the number of repeated uses was counted in the range of activity loss less than 5%, for enzyme immobilized to the chitosan carrier, the immobilized enzyme could be reused for 3 times, and the activity loss was less than 5%. Immobilized to a short-chain amino-type carrier, some enzymes can be reused for 5 times; Immobilized to a long-chain amino-type carrier, the enzyme of some mutants could be reused for 11 times; Immobilized to epoxy-based carrier, some enzymes can be reused for 6 times. The reusable times of mutant immobilized enzyme was significantly higher than that of female parent immobilized enzyme. Some transaminases after covalent immobilization can play catalytic role in 100% organic solvent, some mutants can react in organic solvent after immobilization, and the activity loss is less than 5% after repeated use for 3 times. Playing a catalytic role in 35% methanol solution, some mutants were reused 5 times after immobilization, and the activity loss was less than 5%.

2.5 Metal Ion Chelating Immobilization Method

Porous glass is very suitable for enzyme immobilization because of its inert material and good water permeability. The silanol groups on the glass and channel surface thereof are used as binding sites to bind to the enzyme and achieve immobilization, but the silanol group on the surface of traditional glass has limited density and uneven distribution, high binding steric hindrance to the enzyme, low protein loading (*Science*, 2010, 329, 305-309; *JChromatogr*, 1976, 125, 115-127) and easy to inactivate the enzyme. Covering the inner and outer surface of porous glass with a layer of organic polymer film can form a more favorable environment for enzyme immobilization. (*Langmuir*, 2004, 20, 10639-10647). The polymer film may be further modified as desired to add various functional groups suitable for immobilization to the surface.

The histidine-tagged protein can be purified by solid-phase metal affinity chromatography, histidine residues in the protein can be chelated with metal ions ($Ni^{2+}$, $Co^{2+}$, $Fe^{3+}$) chelated on a water-insoluble matrix, and then the target protein can be eluted with an imidazole-containing buffer (*Nature*, 1975, 258, 598-599). Based on this technology, the histidine-tagged enzyme can be specifically chelated with the carrier with metal ions chelated at the end, and the purpose of immobilization can be achieved. At the same time, the specificity of the method is high, and miscellaneous proteins can hardly be immobilized.

The glass carrier used in the application is coated on the inner and outer surface of porous glass by polymer film, and the polymer film may be hydrophilic polymer such as acrylic polymer, semi-hydrophilic styrene and acrylonitrile polymer and hydrophobic polymer such as chloromethyl styrene polymer. The surface of the film is modified by amino and then acylated by 2, 4-dihydroxyacetophenone, and the hydroxyl of the 2, 4-dihydroxyacetophenone is chelated with metal ions, so that one end of the 2, 4-dihydroxyacetophenone is bound to the carrier and the other end of the 2, 4-dihydroxyacetophenone is chelated with the metal ions through the arm action of the 2, 4-dihydroxyacetophenone, so that the end of the glass carrier is provided with the metal ions and can be affinity bound to the histidine-tagged protein to achieve specific immobilization. (*ChemicalCommunications*, 2014, 50 (65): 9134-7). Chelated metal ions include, but are not limited to, $Ni^{2+}$, $Co^{2+}$ and $Fe^{3+}$. Table 11 below is listed as the carrier suitable for the immobilization of transaminase in the application.

TABLE 11

| Carrier Name | Property | Metal-ion |
| --- | --- | --- |
| EziG-101 | Hydrophilic | $Fe^{3+}$ |
| EziG-102 | Semi-hydrophilic | $Fe^{3+}$ |
| EziG-103 | Hydrophobic | $Fe^{3+}$ |

In the application, transaminases of female parent R416T+T7C+S47C mutant, single point mutants and combined mutants screened on the basis of female parent mutant were immobilized by covalent binding method.

The buffer solution used for preparing the enzyme solution contains 0.4-1 mg/mL of PLP, the pH of the buffer solution is 7.0-8.0, and the buffer salt is $Na_2HPO_4$—$NaH_2PO_4$, Tris-Cl or boric acid-sodium hydroxide.

Covalently immobilized to the porous glass carrier, directly mixing the enzyme solution with carrier, incubating for 40-60 min at 20° C., collecting the precipitate by filtration, and rinsing the precipitate with the buffer.

The prepared immobilized enzyme can be dried by nitrogen blow drying, vacuum drying, freeze drying and so on.

In this application, the transaminase is bound to the carrier by chelation, and the activity recovery is 70%-80%. The immobilized enzyme is recovered by filtration or liquid suction by syringe, which can be reused. Reacting in an aqueous solvent, compared with the first use, the number of reuse times was counted in the range of activity loss less than 5%. For some mutant immobilized enzymes, the immobilized enzyme could be reused for 12 times, and the activity loss was less than 5%; Reacting in organic solvents, compared with the first use, the number of reuse times was counted in the range of activity loss less than 5%. For some mutant immobilized enzymes, the immobilized enzyme could be reused for 8 times.

III. Application Method of Immobilized Transaminase

The immobilized transaminase of the present application can transform the amino acceptors shown in substrate 1 and substrate 2 into the corresponding primary amines, and the amino donor used is isopropylamine.

The immobilized transaminase of the application can be applied in the following solvents: 100% aqueous solution, solvent containing 20%-50% DMSO, solvent containing 35% methanol, or 100% water saturated organic solvent (e.g., may be 100% water saturated methyl tert-butyl ether or 100% water saturated isopropyl acetate).

The immobilized enzyme disclosed by the invention can be applied to batch reactions in a stirring mode, and can also be applied to continuous flow reactions filled in a pipeline reactor.

The batch stirring reaction operation mode is as follows: adding the raw materials, namely the amino acceptor, the amino donor, the immobilized enzyme, the coenzyme PLP and the solvent into the reaction vessel at one time, and reacting for more than 16 h by means of mechanical stirring. After the reaction, the immobilized enzyme was recovered by filtration and applied to the next round of reaction.

The operation mode of the continuous reaction is as follows: filling the immobilized enzyme into a tubular reactor, completely dissolving raw materials, namely an amino acceptor, an amino donor and coenzyme PLP, into a reaction solution with a proper solvent, injecting the reaction solution into the tubular reactor filled with the immobilized enzyme at a proper flow rate with a plunger pump, and receiving a product solution with the solvent at an outlet.

During continuous reaction operation, the solvent can be 35% methanol solution or 100% water-saturated methyl tertiary ether.

The benefits of the present application are further illustrated by the following specific examples.

Example 1: Mutant Tolerance Test at 30° C., pH 9.5 and 50% DMSO

Crude enzyme was treated for 1 h at 30° C., pH 9.5, DMSO concentration of 50%, then 0.1 g substrate 1, 4 eq isopropylamine hydrochloride and 0.6-1 mg PLP (pyridoxal 5'-phosphate) were added to a 10 mL reaction flask, then 5 mg of the treated enzyme was added and thermostatically stirred for 16 h in the environment of 30° C., pH 9.5, DMSO concentration of 50%. The transformation rate was measured by HPLC and the mutant reaction data are shown in Table 12 below.

TABLE 12

| Mutation site | Transformation rate (%) | Mutation site | Transformation rate (%) | Mutation site | Transformation rate (%) |
|---|---|---|---|---|---|
| Female parent R416T + T7C + S47C | 67.7 | K51R | 77.5 | T107F | 92.3 |
| M356L | 80.4 | A95P | 88.6 | T107A | 94.4 |
| F364L | 80.4 | E368P | 97.1 | G110P | 89.2 |
| C404L | 78.7 | Q346E | 92.6 | Q380L | 95.5 |
| M430L | 76.5 | H333K | 87.9 | K193I | 93.5 |
| R405E | 95.4 | D371G | 83.2 | I297L | 96.4 |
| R405A | 85.7 | E246A | 87.2 | R305H | 97.1 |
| K90G | 73.2 | C328A | 93.8 | F111Y | 78.6 |
| K219T | 73.9 | N412G | 80.5 | K190E | 88.7 |
| K69N | 83.9 | G201C | 86.7 | G201C | 86.7 |
| K304D | 90.9 | T402P | 84.3 | A286T | 98.2 |

Example 2: Mutant Tolerance Test at 45° C., pH 10 and 50% DMSO

Crude enzyme was treated for 1 h at 45° C., pH 10, DMSO concentration of 50%, then 0.1 g substrate 1, 4 eq isopropylamine hydrochloride and 0.6-1 mg PLP (pyridoxal 5'-phosphate) were added to a 10 mL reaction flask, then 5 mg of the treated enzyme was added and thermostatically stirred for 16 h in the environment of 45° C., pH 10, DMSO concentration of 50%. The transformation rate was measured by HPLC and the mutant reaction data are shown in Table 13 below.

TABLE 13

| Mutation site | Transformation rate (%) | Mutation site | Transformation rate (%) |
|---|---|---|---|
| Female parent R416T + T7C + S47C | 13.7 | R405E + A95P + K304D + Q380L | 90.7 |
| R405E | 64.3 | R405E + K90G + A95P + K304D + Q380L | 94 |
| A95P | 66.7 | R405E + K90G + A95P + K304D + Q380L + I297 | 97.3 |
| Q380L | 83.5 | R405E + K90G + A95P + K304D + Q380L + E368P | 97.4 |
| I297L | 87.3 | R405E + K90G + A95P + K304D + Q380L + Q346E | 89.3 |
| F111Y | 46.3 | R405E + K90G + A95P + K304D + Q380L + H333K | 90.8 |
| R305H | 37.6 | R405E + K90G + A95P + K304D + Q380L + D371G | 64.1 |
| K190E | 39.8 | R405E + K90G + A95P + K304D + Q380L + C328A | 59.4 |
| K51R + W187Y | 83.1 | R405E + K90G + A95P + K304D + Q380L + T402P | 57.9 |
| R405E + A95P + K304D | 92.1 | R405E + K90G + A95P + K304D + Q380L + T107A | 92.2 |
| K69N | 30.7 | G201C | 28.9 |
| A286T | 92.5 | –/– | –/– |

Example 3: Mutant Tolerance Test at 30° C., pH 8 and 35% Methanol

Crude enzyme was treated for 1 h at 30° C., pH 8, MeOH concentration of 35%, then 0.1 g substrate 1, 4 eq isopropylamine hydrochloride and 0.6-1 mg PLP (pyridoxal 5'-phosphate) were added into a 10 mL reaction flask, then 5 mg of the treated enzyme was added and continued to thermostatically stir for 16 h in the environment of 30° C., pH 8, MeOH concentration of 35%. The transformation rate was measured by HPLC and the mutant reaction data are shown in Table 14 below.

TABLE 14

| Mutation site | Transformation rate | Mutation site | Transformation rate (%) |
|---|---|---|---|
| Female parent R416T + T7C + S47C | 8.9 | R405E + K90G + A95P + K304D + Q380L | 58.5 |
| Q380L | 66.7 | R405E + K90G + A95P + K304D + Q380L + E368P | 91.2 |
| I297L | 60.2 | R405E + K90G + A95P + K304D + Q380L + Q346E | 77.7 |
| F111Y | 28.6 | R405E + K90G + A95P + K304D + Q380L + H333K | 78.2 |
| R305H | 53.1 | R405E + K90G + A95P + K304D + Q380L + C328A | 78.6 |
| K190E | 44.8 | R405E + K90G + A95P + K304D + Q380L + T107A | 83.4 |
| K193I | 60.4 | R405E + K90G + A95P + K304D + Q380L + I297L | 97 |
| R405E + A95P + K304D | 86 | A95P + R405E + K304D + Q380L + K90G + I297L + E368P + T107A | 96 |
| K69N | 34.5 | G201C | 35.1 |
| A286T | 64.3 | R405E + K90G + A95P + K304D + Q380L + I297L + E368P + T107A + A286T | 70.9 |
| R405E + K90G + A95P + K304D + Q380L + I297L + E368P + T107A + K69N | 61.9 | R405E + K90G + A95P + K304D + Q380L + I297L + E368P + T107A + G201C | 64.3 |
| R405E + K90G + A95P + K304D + Q380L + N412G | 40.4 | R405E + K90G + A95P + K304D + Q380L + T402P | 34.5 |
| R405E + K90G + A95P + K304D + Q380L + D371G | 27.8 | –/– | –/– |

Example 4: Mutant Tolerance Test at 45° C., pH 8 and 40% Methanol

Crude enzyme was treated for 1 h at 45° C., pH 8, MeOH concentration of 40%, then 0.1 g substrate 1, 4 eq isopropylamine hydrochloride and 0.6-1 mg PLP (pyridoxal 5'-phosphate) were added into a 10 mL reaction flask, then 5 mg of the treated enzyme was added and continued to thermostatically stir for 16 h in the environment of 45° C., pH 8, MeOH concentration of 40%. The transformation rate was measured by HPLC and the mutant reaction data are shown in Table 15 below.

TABLE 15

| Mutation site | Transformation rate (%) | Mutation site | Transformation rate (%) |
| --- | --- | --- | --- |
| Female parent | 2.9 | R405E + K90G + A95P + K304D + Q380L + I297L + A286T | 96.5% |
| R416T + T7C + S47C | | | |
| R405E + K90G + A95P + K304D + Q380L + I297 | 98.2% | R405E + K90G + A95P + K304D + Q380L + I297L + E368P | 98% |
| R405E + K90G + A95P + K304D + Q380L + I297L + E368P + T107A + K69N | 86.7 | R405E + K90G + A95P + K304D + Q380L + I297L + E368P + T107A + G201C | 87.8 |
| R405E + K90G + A95P + K304D + Q380L + I297L + E368P + T107A | 96% | R405E + K90G + A95P + K304D + Q380L + I297L + E368P + T107A + A286T | 89.8 |

Example 5: Cross-Linking Immobilization 0.1 g enzyme powder was dissolved in 2 mL of phosphate buffer (0.1 M PB, pH 7.0-8.0, containing 0.4-1 mg/mL PLP (pyridoxal 5'-phosphate)), 18 mL ethanol, or 18 mL isopropanol, or ammonium sulfate (final saturation of 90%) was slowly added as a precipitant with stirring in an ice-water bath, and after 10 min of stirring, 1.1-2.7 mL 25% glutaraldehyde solution (final concentration of 200-500 mM) was added, centrifuged or filtered after stirring in the ice-water bath for 30-40 min, the precipitate was washed with a phosphate buffer for three times, stored at 4° C., and directly applied to an aqueous phase reaction. Or the cross-linked enzyme aggregate is lyophilized, and the cross-linked enzyme aggregate lyophilized powder after lyophilization can be applied in aqueous phase and organic phase reactions.

Example 6: Reaction of Cross-Linked Enzyme Aggregates in Aqueous Phase for Testing Activity To a 10 mL reaction flask, 0.3 mL DMSO was added, 0.1 g substrate 1 was dissolved, 4 eq isopropylamine hydrochloride and 1.0 mg PLP (pyridoxal 5'-phosphate) were added, 0.1 M PB 7.0 was added until the final volume of the reaction solution was 1 mL, and 5 mg enzyme or cross-linked enzyme aggregate wet enzyme prepared from 5 mg enzyme or cross-linked enzyme aggregate lyophilized powder was added and stirred at 45° C. for 16 h. The transformation rate was measured by HPLC and reaction data are shown in Table 16 below.

TABLE 16

| Strain number | Immobilization form | Transformation rate (%) | Reuse times with activity loss <5% |
| --- | --- | --- | --- |
| Female parent R416T + T7C + S47C | No | 98.20% | 1 |
| | Cross-linked enzyme wet enzyme | 92.30% | 3 |
| | Cross-linked enzyme lyophilized powder | 86.20% | 1 |
| A95P | No | 97.80% | 1 |
| | Cross-linked wet enzyme | 98.20% | 6 |
| | Cross-linked enzyme lyophilized powder | 92.70% | 5 |
| R405E + K90G + A95P + K304D + Q380L | No | 98.60% | 1 |
| | Cross-linked wet enzyme | 97.90% | 10 |
| | Cross-linked enzyme lyophilized powder | 97.30% | 8 |
| R405E + K90G + A95P + K304D + Q380L + I297L | No | 98.50% | 1 |
| | Cross-linked wet enzyme | 98.30% | 14 |
| | Cross-linked enzyme lyophilized powder | 98.50% | 13 |
| R405E + K90G + A95P + K304D + Q380L + I297L + E368P + T107A | Cross-linked wet enzyme | 98.30% | 13 |
| R405E + K90G + A95P + K304D + Q380L + I297L + E368P + T107A + A286T | Cross-linked wet enzyme | 98.50% | 14 |
| R405E + K90G + A95P + K304D + Q380L + I297L + E368P + T107A + K69N | Cross-linked wet enzyme | 98.00% | 12 |
| R405E + K90G + A95P + K304D + Q380L + H333K | Cross-linked wet enzyme | 98.30% | 12 |
| R405E + K90G + A95P + K304D + Q380L + E368P | Cross-linked wet enzyme | 98.40% | 11 |
| K51R + W187Y | Cross-linked wet enzyme | 98.20% | 9 |
| R405E + K90G + A95P + K304D + Q380L + Q346E | Cross-linked wet enzyme | 98.50% | 10 |
| R405E + K90G + A95P + K304D + Q380L + C328A | Cross-linked wet enzyme | 98.40% | 10 |

Example 7: Reaction of Cross-Linked Enzyme in Organic Phase for Testing Activity To a 10 mL reaction flask, 1 mL water-saturated methyl tert-butyl ether was added, followed by 10 mg substrate 1 and 4 eq isopropylamine, then cross-linked enzyme aggregates lyophilized powder prepared from 10 mg enzyme powder was added, and stirred for 16 h at 30° C. The transformation rate was measured by HPLC and reaction data are shown in Table 17 below.

TABLE 17

| Strain number | Immobilization form | Transformation rate (%) | Reuse times with activity loss <5% |
| --- | --- | --- | --- |
| Female parent R416T + T7C + S47C | Cross-linked enzyme lyophilized powder | 87.90% | 1 |

TABLE 17-continued

| Strain number | Immobilization form | Transformation rate (%) | Reuse times with activity loss <5% |
|---|---|---|---|
| A95P | Cross-linked enzyme lyophilized powder | 90.30% | 3 |
| R405E + K90G + A95P + K304D + Q380L | Cross-linked enzyme lyophilized powder | 90.60% | 3 |
| R405E + K90G + A95P + K304D + Q380L + I297L | Cross-linked enzyme lyophilized powder | 94.70% | 5 |
| R405E + K90G + A95P + K304D + Q380L + I297L + E368P + T107A | Cross-linked enzyme lyophilized powder | 92.10% | 5 |
| R405E + K90G + A95P + K304D + Q380L + I297L + E368P + T107A + A286T | Cross-linked enzyme lyophilized powder | 90.90% | 4 |

Example 8: Reaction of Transaminase Embedded-Crosslinked Immobilized Enzyme in Aqueous Phase for Testing Activity To a 10 mL reaction flask, 0.4 mL DMSO was added (final concentration of DMSO being 40%), 0.1 g substrate 1 was dissolved, 4 eq isopropylamine hydrochloride and 1.0 mg PLP (pyridoxal 5'-phosphate) were added, 0.1 M PB 7.0 was added until the final volume of the reaction solution was 1 mL, and 5 mg enzyme or embedded-crosslinked immobilized enzyme prepared from 5 mg enzyme was added and stirred at 45° C. for 16 h. The transformation rate was measured by HPLC and reaction data are shown in Table 18 below.

TABLE 18

| Mutation site | Immobilization form | Transformation rate (%) | Reuse times with activity loss <5% |
|---|---|---|---|
| Female parent | No | 93.9 | 1 |
| R416T + T7C + S47C | Embedded-crosslinked immobilized enzyme | 54.9 | 8 |
| R405E + K90G + A95P + K304D + Q380L | No | 97.8 | 1 |
| | Covalent immobilized enzyme | 76.4 | 11 |
| R405E + K90G + A95P + K304D + Q380L + I297L + E368P + T107A | No | 98.1 | 1 |
| | Embedded-crosslinked immobilized enzyme | 98.0 | 11 |
| R405E + K90G + A95P + K304D + Q380L + Q346E | No | 97.5 | 1 |
| | Embedded-crosslinked immobilized enzyme | 98.0 | 10 |
| R405E + K90G + A95P + K304D + Q380L + I297L | No | 97.9 | 1 |
| | Covalent immobilized enzyme | 97.6 | 18 |

Example 9: Reaction of Transaminase Embedded-Crosslinked Immobilized Enzyme in 35% Methanol Water Solution for Testing Activity In a 10 mL reaction flask, 0.35 mL methanol (methanol final concentration being 40%) was added, 0.1 g substrate 1 was dissolved, 4 eq isopropylamine hydrochloride and 1.0 mg PLP (pyridoxal 5'-phosphate) were added, 0.1 M PB 7.0 was added until the final volume of the reaction solution was 1 mL, and 10 mg enzyme or embedded-crosslinked immobilized enzyme prepared from 10 mg enzyme was added and stirred at 30° C. for 16 h. The transformation rate was measured by HPLC and reaction data are shown in Table 19 below.

TABLE 19

| Mutation site | Immobilization form | Transformation rate (%) | Reuse times with activity loss <5% |
|---|---|---|---|
| Female parent | No | 60.6 | 1 |
| R416T + T7C + S47C | Embedded-crosslinked immobilized enzyme | 54.9 | 6 |
| R405E + K90G + A95P + K304D + Q380L | No | 98.3 | 1 |
| | Covalent immobilized enzyme | 76.4 | 9 |
| R405E + K90G + A95P + K304D + Q380L + I297L | No | 98.5 | 1 |
| | Covalent immobilized enzyme | 97.6 | 12 |

Example 10: Adsorption Immobilization Method of Transaminase 4 mL PB buffer containing 0.4 mg/mL PLP (100 mM pH 7.0) was added into the carrier, and 0.1 g enzyme was added at the same time, stirred in a low speed of 80 rpm overnight at 20° C. The supernatant was removed, the precipitate was washed 3-4 times with buffer, the supernatant was removed, the precipitate was blown dry with nitrogen, or dried by freeze drying and stored at 4° C.

Example 11: Reaction of Transaminase Adsorptive Immobilized Enzyme in Organic Phase for Testing Activity In a 10 mL reaction flask, 1 mL water-saturated methyl tert-butyl ether was added, followed by 10 mg substrate 1 and 4 eq isopropylamine, then immobilized transaminase prepared from 20 mg enzyme was added, and stirred for 16 h at 30° C. The transformation rate was measured by HPLC and reaction data are shown in Table 20 below.

TABLE 20

| Mutation site | Immobilization form | Carrier | Transformation rate (%) | Reuse times with activity loss <5% |
|---|---|---|---|---|
| Female parent R416T + T7C + S47C | Adsorption immobilized enzyme | Diaion HP2MG | 64.3 | 2 |
| | | X17S0401 | 57.2 | 2 |
| | | EXE120 | 53.9 | 2 |

TABLE 20-continued

| Mutation site | Immobilization form | Carrier | Transformation rate (%) | Reuse times with activity loss <5% |
|---|---|---|---|---|
| | | ECR8806 | 60.2 | 3 |
| | | ECR1030 | 49.2 | 2 |
| | | ECR1090 | 43.8 | 1 |
| R405E + K90G + A95P + K304D + Q380L + I297L | Adsorption immobilized enzyme | Diaion HP2MG | 91.4 | 4 |
| | | X17S0401 | 89.2 | 4 |
| | | EXE120 | 90.7 | 4 |
| | | ECR8806 | 94.8 | 6 |
| | | ECR1030 | 79.9 | 3 |
| | | ECR1090 | 72.4 | 3 |
| R405E + K90G + A95P + K304D + Q380L + H333K | Adsorption immobilized enzyme | ECR8806 | 92.4 | 4 |
| R405E + K90G + A95P + K304D + Q380L + Q346E | Adsorption immobilized enzyme | ECR8806 | 94.7 | 4 |
| R405E + K90G + A95P + K304D + Q380L + N412G | Adsorption immobilized enzyme | ECR8806 | 82.8 | 3 |
| R405E + K90G + A95P + K304D + Q380L + I297L + E368P + T107A | Adsorption immobilized enzyme | ECR8806 | 96.8 | 6 |
| R405E + K90G + A95P + K304D + Q380L + I297L + E368P + T107A + A286T | Adsorption immobilized enzyme | ECR8806 | 76.3 | 5 |
| R405E + K90G + A95P + K304D + Q380L + I297L + E368P + T107A + G201C | Adsorption immobilized enzyme | ECR8806 | 81.5 | 5 |

Example 12: Immobilization of Transaminase with Chitosan as Carrier

Preparation of chitosan carrier: 5 g chitosan (molecular weight 300 KDa-500 KDa) was added to 250 mL 1% acetic acid solution and dissolved by heating in microwave oven to prepare aqueous phase. The oil phase was prepared by evenly mixing 300 mL toluene with 2.2 g Span 80, 1.2 mL n-hexanol and stirring at room temperature for 2 h. An aqueous phase was slowly dropwise adding into an oil phase under stirring to prepare an emulsion, the emulsion was poured into a 1.5 L 12% NaOH solution, stirred for 3 h, 1 L ethanol was added, filtered, a filter cake was thoroughly cleaned with purified water to obtain about 40 g wet carrier, the wet carrier is soaked in 140 mL pure water, and stored at 4° C.

Activating a carrier: 1.1 mL 25% glutaraldehyde (final glutaraldehyde concentration of 2.5%) was added per milliliter of wet carrier.

Immobilization: 0.2 g enzyme was added into the activated carrier, stirred for 6 h at 20-25° C., the carrier was washed, centrifuged to remove the supernatant, and the precipitate is the immobilized enzyme, and storing at 4° C.

Example 13: Immobilization of Transaminase on C6 Amino Carrier

Activating a carrier: 1 g carrier ECR8409 was washed 1-2 times with 20 mM low ionic strength buffer, the supernatant was removed, 4 mL 2% glutaraldehyde (prepared from 20 mM low ionic strength buffer dilution reagent and 25% glutaraldehyde), at 20° C., activated at 80 rpm for 1 h, washed 1-2 times with 20 mM buffer, and the supernatant was removed.

Immobilization: 4 mL PB buffer containing 0.4 mg/mL PLP (20 mM pH 7.0) was added into the activated carrier, and 0.1-0.2 g enzyme was added at the same time, stirred in a low speed of 80 rpm overnight at 20° C. The supernatant was removed, the precipitate was washed 3-4 times with buffer, the supernatant was removed, and the precipitate was blown dry with nitrogen, or dried by freeze drying and stored at 4° C.

Example 14: Immobilization of Transaminase on Epoxy Carrier 1 g carrier ECR8285 was washed 1-2 times with 100 mM PB buffer, the clear liquid was removed, 4 mL Buffer (100 mM PB, pH 7.0, containing 1 M NaCl) was added, 0.1 g-0.2 g enzyme was added at the same time, at 20° C., stirred at low speed of 80 rpm overnight (18-20 h), and then stood at 4° C. for 20 h. The supernatant was removed and the precipitate was washed 3-4 times with Buffer, blown dry with nitrogen and stored for 4° C.

Example 15: Reaction of Covalent Immobilized Transaminase in Aqueous Phase for Testing Activity In a 10 mL reaction flask, 04 mL DMSO (DMSO final concentration being 40%) was added, 0.1 g substrate 1 was dissolved, 4 eq isopropylamine hydrochloride and 1.0 mg PLP (pyridoxal 5'-phosphate) were added, 0.1 M PB7.0 was added until the final volume of the reaction solution was 1 mL, and 5 mg enzyme or immobilized transaminase prepared from 5 mg enzyme was added and stirred at 45° C. for 16 h. The transformation rate was measured by HPLC and reaction data are shown in Table 21 below.

TABLE 21

| Mutation site | Immobilization form | Carrier | Transformation rate (%) | Reuse times with activity loss <5% |
|---|---|---|---|---|
| Female parent | No | No | 60.6 | 1 |
| R416T + T7C + S47C | Covalent immobilized enzyme | Chitosan | 36.1 | 3 |
| | | ECR8309 | 32.8 | 2 |
| | | ECR8409 | 41.5 | 3 |
| | | ECR8285 | 31.7 | 2 |
| A95P | No | No | 97.8 | 1 |
| | Covalent immobilized enzyme | Chitosan | 65.2 | 3 |
| | | ECR8309 | 63.7 | 5 |
| | | ECR8409 | 78.4 | 6 |
| | | ECR8285 | 57.2 | 4 |
| R405E + K90G + A95P + K304D + Q380L | No | No | 98.3 | 1 |
| | Covalent immobilized enzyme | Chitosan | 76.4 | 4 |
| | | ECR8309 | 72.1 | 5 |
| | | ECR8409 | 88.6 | 11 |
| | | ECR8285 | 69.2 | 6 |
| R405E + K90G + A95P + K304D + Q380L + I297L | No | No | 98.5 | 1 |
| | Covalent immobilized enzyme | ECR8409 | 97.6 | 12 |
| Q380L | No | No | 97.8 | 1 |
| | Covalent immobilized enzyme | ECR8409 | 87.6 | 7 |
| R405E | No | No | 97.1 | 1 |
| | Covalent immobilized enzyme | ECR8409 | 89.5 | 6 |

TABLE 21-continued

| Mutation site | Immobilization form | Carrier | Transformation rate (%) | Reuse times with activity loss <5% |
|---|---|---|---|---|
| K51R + W187Y | No | No | 96.8 | 1 |
|  | Covalent immobilized enzyme | ECR8409 | 83.3 | 6 |
| R405E + A95P + K304D | No | No | 97.6 | 1 |
|  | Covalent immobilized enzyme | ECR8409 | 88.9 | 8 |
| R405E + K90G + A95P + K304D + Q380L + E368P | No | No | 98.1 | 1 |
|  | Covalent immobilized enzyme | ECR8409 | 90.3 | 11 |

Example 16: Reaction of Covalent Immobilized Transaminase in 35% Methanol Water Solution for Testing Activity In a 10 mL reaction flask, 0.35 mL methanol (methanol final concentration being 40%) was added, 0.1 g substrate 1 was dissolved, 4 eq isopropylamine hydrochloride and 1.0 mg PLP (pyridoxal 5'-phosphate) were added, 0.1 M PB 7.0 was added until the final volume of the reaction solution was 1 mL, and 10 mg enzyme or immobilized transaminase prepared from 10 mg enzyme was added and stirred at 30° C. for 16 h. The transformation rate was measured by HPLC and reaction data are shown in Table 22 below.

TABLE 22

| Strain number | Immobilization form | Carrier | Transformation rate (%) | Reuse times with activity loss <5% |
|---|---|---|---|---|
| Female parent | No | No | 30.1 | 1 |
| R416T + T7C + S47C | Covalent immobilized enzyme | ECR8409 ECR8285 | 23.7 17.6 | 2 2 |
| A95P | No | No | 67.3 | 1 |
|  | Covalent immobilized enzyme | ECR8409 | 47.7 | 4 |
| R405E + K90G + A95P + K304D + Q380L | No | No | 83.7 | 1 |
|  | Covalent immobilized enzyme | ECR8409 | 64.8 | 5 |
| R405E + K90G + A95P + K304D + Q380L + I297L | No | No | 97.5 | 1 |
|  | Covalent immobilized enzyme | ECR8409 | 92.3 | 5 |
| R405E + K90G + A95P + K304D + Q380L + H333K | No | No | 95.9 | 1 |
|  | Covalent immobilized enzyme | ECR8409 | 90.8 | 4 |
| R405E + K90G + A95P + K304D + Q380L + I297L + E368P + T107A | No | No | 96.7 | 1 |
|  | Covalent immobilized enzyme | ECR8409 | 93.1 | 4 |
| R405E + K90G + A95P + K304D + Q380L + I297L + E368P + T107A + A286T | No | No | 97.1 | 1 |
|  | Covalent immobilized enzyme | ECR8409 | 93.3 | 5 |

Example 17: Reaction of Covalent Immobilized Transaminase in Organic Phase for Testing Activity In a 10 mL reaction flask, 1 mL water-saturated isopropyl acetate was added, followed by 10 mg substrate 1 and 4 eq isopropylamine, then 20 mg enzyme or immobilized transaminase prepared from 20 mg enzyme was added, and stirred for 16 h at 30° C. The transformation rate was measured by HPLC and reaction data are shown in Table 23 below.

TABLE 23

| Strain number | Immobilization form | Carrier | Transformation rate (%) | Reuse times with activity loss <5% |
|---|---|---|---|---|
| Female parent | Covalent immobilized enzyme | ECR8409 | 42.2 | 3 |
| R416T + T7C + S47C | Covalent immobilized enzyme | ECR8285 | 23.7 | 2 |
| A95P | Covalent immobilized enzyme | ECR8409 | 55.1 | 3 |
| R405E + K90G + A95P + K304D + Q380L | Covalent immobilized enzyme | ECR8409 | 72.3 | 3 |
| R405E + K90G + A95P + K304D + Q380L + I297L | Covalent immobilized enzyme | ECR8409 | 94.5 | 3 |

Example 18: Continuous Reaction of Covalent Immobilized Enzyme in Transaminase Packed Bed (Methanol as Cosolvent for Substrate)

75 g immobilized enzyme prepared by mutant R405E+K90G+A95P+K304D+Q380L+I297L immobilized to ECR8409 carrier was filled into the reactor, the column volume (CV) was 150 mL, and 2CV buffer (0.1 M PB 7.0 containing 5 mg/mL PLP, 2 M isopropylamine hydrochloride) was injected into the packed bed with a plunger pump. The formulated reaction solution (0.5 M substrate 1, 2 M isopropylamine hydrochloride, 5 mg/mL PLP, 35% MeOH) was injected into a packed bed with a plunger pump, 40° C. water bath, a flow rate of 0.25 mL/min, retention time of about 600 min, transformation rate>98%, and a continuous operation for 240 h with no reduction in transformation rate.

Example 19: Glass Carrier Chelating Immobilized Transaminase 1 g EziG-101, EziG-102 or EziG-103 porous glass carriers were washed 1-2 times with buffer (20 mM Tris-Cl 8.5), the supernatant was removed, 20 mL Buffer was added to the carriers meanwhile enzyme powder or enzyme solution was added, stirred at 80 rpm for 1 h at 20° C., the supernatant was removed, the precipitate was washed 3-4 times with Buffer, filtered and dried under vacuum, and stored at 4° C.

Example 20: Reaction of Immobilized Transaminase Chelated on EziG-101 Porous Glass Carrier in Aqueous Phase for Testing Activity In a 10 mL reaction flask, 0.2 mL DMSO was added, 0.1 g substrate 1 was dissolved, 4 eq isopropylamine hydrochloride and 0.5 mg PLP (pyridoxal 5'-phosphate) were added, 0.1 M PB 7.0 was added until the final volume of the reaction solution was 1 mL, and 0.1 g enzyme powder or immobilized transaminase prepared from 0.1 g enzyme powder by EziG-101 carrier chelating method was added and stirred at 45° C. for 16 h. The transformation rate was measured by HPLC and reaction data are shown in Table 24 below.

TABLE 24

| Mutant | Immobilization form | Transformation rate (%) | Reuse times with activity loss <5% |
|---|---|---|---|
| Female parent | No | 98.7 | 1 |
| R416T + T7C + S47C | Chelating immobilized enzyme | 98.2 | 4 |
| A95P | No | 98.5 | 1 |
|  | Chelating immobilized enzyme | 98.6 | 7 |
| R405E + K90G + A95P + K304D + Q380L | No | 98.4 | 1 |
|  | Chelating immobilized enzyme | 98.2 | 11 |
| R405E + K90G + A95P + K304D + Q380L + I297L | No | 98.5 | 1 |
|  | Chelating immobilized enzyme | 98.2 | 12 |
| R405E + K90G + A95P + K304D + Q380L + I297L + E368P + T107A + G201C | No | 98.2 | 1 |
|  | Chelating immobilized enzyme | 98.0 | 12 |
| R405E + K90G + A95P + K304D + Q380L + I297L + E368P + T107A + A286T | No | 98.2 | 1 |
|  | Chelating immobilized enzyme | 98.2 | 12 |

Example 21: Reaction of Immobilized Transaminase Chelated on Porous Glass Carrier in Organic Phase for Testing Activity In a 10 mL reaction flask, 1 mL water-saturated methyl tert-butyl ether was added, followed by 10 mg substrate 1 and 4 eq isopropylamine, then 20 mg enzyme or immobilized transaminase prepared from 20 mg enzyme was added, and stirred for 16 h at 30° C. The transformation rate was measured by HPLC and reaction data are shown in Table 25 below.

TABLE 25

| Mutation site | Immobilization form | Carrier | Transformation rate (%) | Reuse times with activity loss <5% |
|---|---|---|---|---|
| Female parent | Chelating immobilized enzyme | EziG-101 | 69.8 | 4 |
| R416T + T7C + S47C |  | EziG-102 | 59.9 | 3 |
|  |  | EziG-103 | 68.1 | 4 |
| R405E + K90G + A95P + K304D + Q380L + I297L | Chelating immobilized enzyme | EziG-101 | 92.4 | 6 |
|  |  | EziG-102 | 89.2 | 6 |
|  |  | EziG-103 | 91.6 | 8 |

As can be seen from the above examples, the mutant with improved activity, stability, tolerance to temperature, pH and organic solvent obtained through directional evolution screening in the present application not only reduces the amount of enzyme used in production application, but also greatly improves the possibility of preparing various immobilized enzymes. In addition, in the present application by immobilizing (self-crosslinking or covalent bonding with a carrier) the transaminase subjected to directed evolution, the application of the immobilized transaminase in aqueous phase reaction and organic phase reaction is realized, so that the enzyme is easy to separate from a reaction system, the emulsification phenomenon caused by residual enzyme protein in the post-reaction treatment process is reduced, and meanwhile, the immobilized transaminase mutant can endure all kinds of extreme environment with low activity loss and high reuse times, thus realized the continuous transamination of substrate 1 and substrate 2.

The above are only preferred examples of the present application and are not intended to limit the present application. For those skilled in the art, the present application may have various modifications and changes. Any modification, equivalent replacement, improvement, etc. made within the spirit and principle of the present application should be included in the protection scope of the present application.

What is claimed is:

1. A transaminase mutant, comprising a protein having the amino acid sequence of SEQ ID NO: 1 with the exception of a mutation of more amino acids; wherein the mutation of more amino acids selected from the group consisting of: T7C+S47C, T7C+S47C+M356L, T7C+S47C+F364L, T7C+S47C+C404L, T7C+S47C+M430L, T7C+S47C+R405E/A, T7C+S47C+K90G, T7C+547C+K219T, T7C+S47C+K304D, T7C+S47C+K51R, T7C+S47C+A95P, T7C+S47C+E368P, T7C+S47C+Q346E, T7C+S47C+H333K, T7C+S47C+D371G, T7C+S47C+E246A, T7C+S47C+C328A, T7C+S47C+N412G, T7C+S47C+T402P, T7C+S47C+T107F/A, T7C+S47C+G110P, T7C+S47C+K69N, T7C+S47C+G201C, T7C+S47C+Q380L, T7C+S47C+K193I, T7C+S47C+I297L, T7C+S47C+R305H, T7C+S47C+F111Y, T7C+S47C+K190E, T7C+S47C+A286T, T7C+S47C+K51R+W187Y, T7C+S47C+R405E+A95P, T7C+S47C+R405E+A95P+K304 D, T7C+S47C+R405E+A95P+K304D+Q380 L, T7C+S47C+R405E+K90G+A95P+K304D+Q380L, T7C+S47C+R405E+K90G+A95P+K304 D+Q380L+E368P, T7C+S47C+R405E+K90G+A95P+K304D+Q380L+Q346E, T7C+S47C+R405E+K90G+A95P+K304D+Q380L+H333K, T7C+S47C+R405E+K90G+A95P+K304D+Q380L+D371G, T7C+S47C+R405E+K90G+A95P+K304 D+Q380L+E246A, T7C+S47C+R405E+K90G+A95P+K304D+Q380L+C328A, T7C+S47C+R405E+K90G+A95P+K304D+Q380L+N412 G, T7C+S47C+R405E+K90G+A95P+K304D+Q380L+T402P, T7C+S47C+R405E+K90G+A95P+K304D+Q380L+T107F, T7C+S47C+R405E+K90G+A95P+K304D+Q380L+T107A, T7C+S47C+R405E+K90G+A95P+K304D+Q380L+G110P, T7C+S47C+R405E+K90G+A95P+K304D+Q380L+I297L, T7C+S47C+R405E+K90G+A95P+K304D+Q380L+I297L+E368P+T107A, T7C+S47C+R405E+K90G+A95P+K304D+Q380L+I297L+A286T, T7C+S47C+R405E+K90G+A95P+K304D+Q380L+I297L+E368P, T7C+S47C+R405E+K90G+A95P+K304D+Q380L+I297L+E368P+T107A+K69N, T7C+S47C+R405E+K90G+A95P+K304D+Q380L+I297L+E368P+T107A+G201C and T7C+S47C+R405E+K90G+A95P+K304D+Q380L+I297L+E368P+T107A+A286T, wherein "I" represents "or", and having transaminase activity.

2. An immobilized transaminase, wherein the immobilized transaminase comprises the transaminase mutant according to claim 1.

3. The immobilized transaminase according to claim 2, wherein the immobilized transaminase is a transaminase cross-linked enzyme aggregate of the transaminase mutant; wherein the transaminase mutant is precipitated to obtain a transaminase aggregate, and a free amino, a phenolic, an imidazolyl, or a sulfhydryl in the transaminase aggregate is crosslinked with a cross-linking agent to obtain the transaminase cross-linked enzyme aggregate, wherein the cross-linking agent is selected from any one of glutaraldehyde, N, N-methylene biacrylamide, bismaleimide and dextran;
wherein a molecular weight of the dextran is 6 KDa~200 KDa;
wherein the transaminase mutant is precipitated by ethanol to obtain the transaminase aggregate;
wherein a free amino group in the transaminase aggregate is cross-linked with glutaraldehyde to obtain the transaminase cross-linked enzyme aggregate.

4. The immobilized transaminase according to claim 2, wherein the immobilized transaminase is a transaminase embedded-crosslinked immobilized enzyme;
wherein a free amino group in the transaminase mutant and glutaraldehyde form a Schiff base through cross-linking to obtain a transaminase cross-linked enzyme, the transaminase cross-linked enzyme is embedded into a polyacrylamide gel grid to obtain the transaminase embedded-crosslinked immobilized enzyme.

5. The immobilized transaminase according to claim 2, wherein the immobilized transaminase is a covalent immobilized enzyme in which the transaminase mutant is covalently connected with a carrier;
wherein the carrier is a chitosan carrier or a resin carrier;
more wherein the chitosan carrier is covalently bound to the transaminase mutant through a hydroxyl and/or an amino group to form the covalent immobilized enzyme;
more wherein the resin carrier comprises a matrix and a functional group connected with the matrix, wherein the matrix is selected from any of a styrene and methacrylate copolymer, a polystyrene resin and a polymethacrylate resin, and the functional group connected with the matrix is selected from a C2 short-chain amino group, a C4 medium chain amino group, and a C6 long-chain amino group or a epoxy group; and
wherein the resin carrier is selected from ECR8309, ECR8315, EC-HFA, LX-1000HA, LX-1000EA, ECR8409, ECR8415, EC-EP, EC EP403, EXE119, LX-1000EP, Immobead-150A, Immobead-150P, Immobead350A, ECR8206, ECR8209, ECR8215 or ECR8285.

6. The immobilized transaminase according to claim 2, wherein the immobilized transaminase is a chelating immobilized enzyme formed by chelating a transaminase mutant and a carrier through metal ions;
wherein the carrier is a porous glass carrier; and wherein the porous glass carrier is EziG-101, EziG-102 or EziG-103.

7. The immobilized transaminase according to claim 2, wherein the immobilized transaminase is an adsorptive immobilized enzyme formed by physical adsorption between the transaminase mutant and the carrier.

8. A method for producing a chiral amine, comprising a step of transamination reaction between a ketone compound and an amino donor catalyized by a transaminase, wherein the transaminase is the transaminase mutant according to claim 1.

9. The method according to claim 8, wherein the method is a batch reaction; and wherein a reaction system of the batch reaction is an aqueous phase reaction system.

10. The method according to claim 8, the method is a continuous reaction; and wherein a reaction system of the continuous reaction is an organic phase reaction system.

11. The method according to claim 8, wherein the ketone compound is

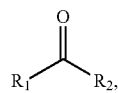

wherein R1 and R2 are each dependently a C1~C8 alkyl, a C5~C10 cycloalkyl, a C6~C10 aryl or a C5~C10 heteroaryl, or R1 and R2 together with the carbon on a carbonyl form a C5~C10 heterocyclyl, a C5~C10 carbocyclyl or a C5~C10 heteroaryl, one or more of heteroatoms in the 05~010 heterocyclyl and 05~010 heteroaryl are respectively selected from at least one of nitrogen, oxygen and sulfur, and the aryl in 06~010 aryl, the heteroaryl in 05~010 heteroaryl, the carbocyclyl in the C5~O10 carbocyclyl or the heterocyclyl in the C5~O10 heterocyclyl is independently unsubstituted or substituted by at least one radical of halogen, alkoxy or alkyl; wherein the ketone compound is

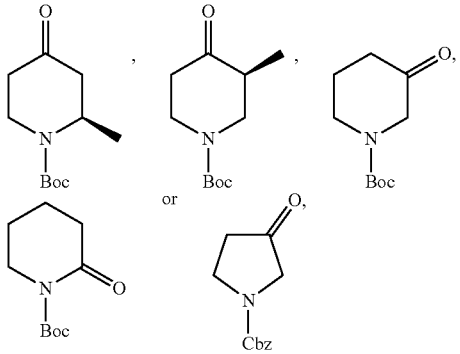

wherein a product of the transamination reaction is

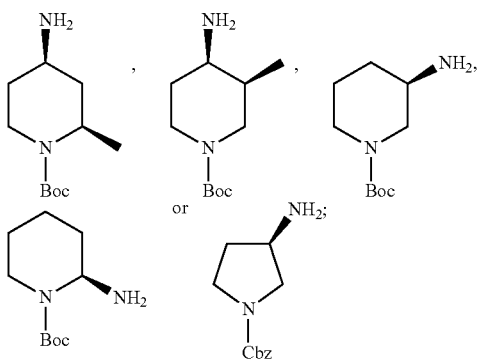

preferably the amino donor is isopropyl amine.

12. The immobilized transaminase according to claim 3, wherein the transaminase cross-linked enzyme aggregate is a cross-linked enzyme aggregate of a transaminase mutant having the amino acid sequence of SEQ ID NO: 1 with the exception of a mutation of more amino acids; wherein the mutation of more amino acids selected from the group consisting of: T7C+S47C, T7C+S47C+A95P, T7C+S47C+R405E+K90G+A95P+K304D+Q380L, T7C+S47O+R405E+K90G+A95P+K304D+Q380L+I297 L+E368P+T107A, T7C+S47O+R405E+K90G+A95P+K304D+Q380L+I297 L+E368P+T107A A286T, T7C+S47O+R405E+K90G+A95P+K304D+Q380L+I297 L+E368P+T107A+K69N, T7C+S47O+R405E+K90G+A95P+K304D+Q380L+H333K, T7C+S47O+R405E+K90G+A95P+K304 D+Q380L+E368P, T7C+S47C+K51R+W187Y, T7C+S47C+R405E+K90G+A95P+K304D+Q380L+Q346E, T7C+S47C+R405E+K90G+A95P+K304D+Q380L+O328A and T7C+S47C+R405E+K90G+A95P+K304D+Q380L+I297L, and having transaminase activity.

13. The immobilized transaminase according to claim 4, wherein the transaminase embedded-crosslinked immobilized enzyme is an embedded crosslinked immobilized enzyme of the transaminase mutant having the amino acid sequence of SEQ ID NO: 1 with the exception of a mutation of more amino acids; wherein the mutation of more amino acids selected from the group consisting of: T7C+S47C, T7C+S47C+R405E+K90G+A95P+K304D+Q380L, T7C+S47C+R405E+K90G+A95P+K304D+Q380L+I297L+E368P+T107A, T7C+S47C+R405E+K90G+A95P+K304D+Q380L+Q346E, and T7C+S47C+R405E+K90G+A95P+K304D+Q380L+I297L, and having transaminase activity.

14. The immobilized transaminase according to claim 5, wherein the covalent immobilized enzyme is a covalent immobilized enzyme of the transaminase mutant having the amino acid sequence of SEQ ID NO: 1 with the exception of a mutation of more amino acids; wherein the mutation of more amino acids selected from the group consisting of: T7C+S47C, T7C+S47C+A95P, T7C+S47C+Q380L, T7C+S47C+R405E, T7C+S47C+K51R+W187Y, T7C+S47C+R405E+A95P+K304D, T7C+S47C+R405E+K90G+A95P+K304D+Q380L+E368P, T7C+S47C+R405E+K90G+A95P+K304D+Q380L, T7C+S47C+R405E+K90G+A95P+K304D+Q380 L+I297L, T7C+S47C+R405E+K90G+A95P+K304D+Q380L+H333K, T7C+S47C+R405E+K90G+A95P+K304D+Q380L+I297L+E368P+T107A and T7C+S47C+R405E+K90G+A95P+K304D+Q380L+I297L+E368P+T107A+A286T, and having transaminase activity.

15. The immobilized transaminase according to claim 6, wherein the chelating immobilized enzyme is a chelating immobilized enzyme of the transaminase mutant having the amino acid sequence of SEQ ID NO: 1 with the exception of a mutation of more amino acids; wherein the mutation of more amino acids selected from the group consisting of: T7C+S47C, T7C+S47C+A95P, T7C+S47C+R405E+K90G+A95P+K304D+Q380L, T7C+S47C+R405E+K90G+A95P+K304D+Q380L+I297L, T7C+S47C+R405E+K90G+A95P+K304D+Q380L+I297L+E368P+T107A+G201C and T7C+S47C+R405E+K90G+A95P+K304D+Q380L+I297L+E368P+T107A+A286T, and having transaminase activity.

16. The immobilized transaminase according to claim 7, wherein the adsorptive immobilized enzyme is an adsorptive immobilized enzyme of the transaminase mutant having the amino acid sequence of SEQ ID NO: 1 with the exception of a mutation of more amino acids; wherein the mutation of more amino acids selected from the group consisting of: T7C+S47C, T7C+S47C+A95P, T7C+547C+R405E+K90G+A95P+K304D+Q380L+I297L, T7C+S47C+R405E+K90G+A95P+K304D+Q380L+H333K, T7C+S47C+R405E+K90G+A95P+K304D+Q380L+Q346E, T7C+S47C+R405E+K90G+A95P+K304D+Q380L+N412G, T7C+547C+R405E+K90G+A95P+K304 D+Q380L+I297L+E368P+T107A, T7C+547C+R405E+K90G+A95P+K304D+Q380L+I297L+E368P+T107A+A286T and T7C+547C+R405E+K90G+A95P+K304D+Q380L+I297L+E368P+T107A+G201C, and having transaminase activity.

17. The immobilized transaminase according to claim 7, wherein the carrier is a resin carrier.

18. The immobilized transaminase according to claim 7, wherein the resin carrier comprises a matrix and a functional group connected with the matrix, wherein the matrix is selected from any of a styrene and methacrylate copolymer, a polystyrene resin and a polymethacrylate resin, and the functional group connected with the matrix is an octadecyl; wherein the resin carrier is selected from ECR8806, ECR1030, ECR1090, ECR1061, ECR1091, ECR8804, Immobead-EC1, lmmobead-5605, lmmobead-5861, X1750409, EXE120 or Diaion HP2MG.

* * * * *